(12) United States Patent
Haji Begli et al.

(10) Patent No.: US 11,697,642 B2
(45) Date of Patent: Jul. 11, 2023

(54) HMF PREPARATION CATALYSED BY ANOLYTE FRACTION

(71) Applicant: SÜDZUCKER AG, Mannheim (DE)

(72) Inventors: Alireza Haji Begli, Ramsen (DE); Christine Kröner, Kindenheim (DE); Waldemar Tschilingiri, Worms (DE); Ralf Riemenschnitter, Carlsberg (DE); Kay Mantyk, Obrigheim (DE)

(73) Assignee: SÜDZUCKER AG, Mannheim (DE)

( * ) Notice: Subject to any disclaimer, the term of this patent is extended or adjusted under 35 U.S.C. 154(b) by 166 days.

(21) Appl. No.: 17/058,560

(22) PCT Filed: May 28, 2019

(86) PCT No.: PCT/EP2019/063851
§ 371 (c)(1),
(2) Date: Nov. 24, 2020

(87) PCT Pub. No.: WO2019/229077
PCT Pub. Date: Dec. 5, 2019

(65) Prior Publication Data
US 2021/0214327 A1    Jul. 15, 2021

(30) Foreign Application Priority Data
May 29, 2018 (DE) .......................... 102018208507.2

(51) Int. Cl.
C07D 307/54    (2006.01)
C07D 307/50    (2006.01)

(52) U.S. Cl.
CPC ......... *C07D 307/54* (2013.01); *C07D 307/50* (2013.01)

(58) Field of Classification Search
CPC ........................... C07D 307/54; C07D 307/50
USPC ...................................................... 549/485
See application file for complete search history.

(56) References Cited

U.S. PATENT DOCUMENTS

| | | |
|---|---|---|
| 4,395,316 A | 7/1983 | St. John |
| 9,598,780 B2 | 3/2017 | Choi et al. |
| 2011/0082304 A1 | 4/2011 | Gruter et al. |
| 2011/0130561 A1 | 6/2011 | Miyashita |
| 2011/0272291 A1 | 11/2011 | Stapley et al. |
| 2014/0315262 A1 | 10/2014 | Sanborn et al. |
| 2014/0349351 A1 | 11/2014 | Jensen et al. |
| 2016/0237576 A1 | 8/2016 | Choi et al. |

FOREIGN PATENT DOCUMENTS

| | | |
|---|---|---|
| CN | 1458905 A | 11/2003 |
| CN | 102933567 A | 2/2013 |
| CN | 103974943 A | 8/2014 |
| DE | 36 01 281 A1 | 7/1987 |
| DE | 69104226 T2 | 9/1993 |
| DE | 10 2014 220 517 A1 | 4/2016 |
| JP | 2015-209411 A | 11/2015 |
| JP | 2016034926 A | 3/2016 |
| JP | 2017-000110 A | 1/2017 |
| WO | 2013106136 A1 | 7/2013 |
| WO | 2015113060 A2 | 7/2015 |

OTHER PUBLICATIONS

International Preliminary Report on Patentability for PCT/EP2019/063851 dated Dec. 10, 2020, 7 pages.
International Search Report and Written Opinion for PCT/EP2019/063851 dated Sep. 16, 2019, with English translation, 10 pages.
European Search Report and Opinion dated Oct. 14, 2022 for EP Application No. 22175244.7. 7 pages.
Qi, et al. Efficient Catalytic Conversion of Fructose into 5-Hydroxymethylfurfural in Ionic Liquids at Room Temperature. ChemSusChem. 2009; 2:944-946.
Caruso, et al. Electrogenerated acid as an efficient catalyst for the preparation of 5-hydroxymethylfurfural. Electrochemistry Communications. Sep. 2010; 12(9):1149-1153.
Watanabe, et al. Continuous Process for HMF Production from Cellulose with Ionic Liquid ([Bmlm]Cl)-Water Mixtures, Journal of the Japan Institute of Energy. 2017; vol. 96, No. 10, pp. 417-429.

*Primary Examiner* — Kristin A Vajda
(74) *Attorney, Agent, or Firm* — Sheppard Mullin Richter & Hampton LLP

(57) ABSTRACT

The present invention relates to a method for the production of 5-hydroxymethylfurfural (HMF), which converts a fructose-containing component using a catalytically active anolyte fraction, which has been produced by electrolysis of water, at a temperature of 90 to 200° C. and for obtaining an HMF-containing product mixture, wherein advantageously a high HMF selectivity is achieved with significantly lower by-product formation.

26 Claims, 5 Drawing Sheets

HMF PREPARATION CATALYSED BY ANOLYTE FRACTION

CROSS-REFERENCE TO RELATED APPLICATIONS

This application is a U.S. National Stage Application under 35 U.S.C. § 371 of International Application No. PCT/EP2019/063851, filed May 28, 2019, which claims priority to DE 102018208507.2, filed May 29, 2018, the contents of which are incorporated to the present disclosure by reference.

The present invention relates to a method for the production of 5-hydroxymethylfurfural (HMF), which converts a fructose-containing component using a catalytically active anolyte fraction, which has been produced by electrolysis of water, which converts the fructose-containing component at a temperature of 90 to 200° C. and leads to obtaining an HMF-containing product mixture, wherein at the same time advantageously a high HMF selectivity is achieved with significantly lower formation of byproducts.

5-Hydroxymethylfurfural (HMF) is a multifunctional molecule with an aromatic 5-ring system, an aldehyde group and an alcohol group. The many functionalities make the molecule a platform chemical that lends itself to many different applications and can serve as the basis for a large number of other compounds. The compounds that can be produced on the basis of HMF firstly include chemicals such as caprolactam or adipic acid, that are already presently being produced via bulk production using petrochemical methods, but also compounds such as 2,5-furandicarboxylic acid (FDCA) which can be used for a large range of applications, for which no technical production method is presently available.

Despite the great potential of HMF and FDCA there has been a lack of economical, technically established production methods for these compounds. The multifunctionality of HMF as one of the greatest advantages of the molecule has also proven to be a major disadvantage in terms of its synthesis with regard to the secondary chemical processes which may subsequently occur as a result of this multifunctionality. Especially in aqueous systems, HMF is not stable under the reaction conditions necessary for the synthesis (acidic pH value, elevated temperature) and, firstly, HMF reacts under polymerization with itself and/or the starting materials and intermediate products to form so-called humins, which are soluble or insoluble depending on the chain length and lead to a brown to black coloration of the reaction solution. Another undesirable secondary reaction is the acid-catalyzed rehydration of HMF to form levulinic and formic acid, wherein levulinic acid in particular can react with HMF to form further undesirable byproducts. For the most economical production of HMF, it is therefore absolutely necessary to avoid the occurrence of this secondary reaction and the secondary reaction of HMF and levulinic acid as far as possible.

In principle, a distinction can be made between single-phase and two-phase reaction systems in the numerous different synthetic routes that have been described in the prior art for the production of HMF. Both approaches can use both homogeneous and heterogeneous catalysts. In the single-phase systems, the HMF synthesis can be carried out not only in purely aqueous systems but also in organic solvents, such as DMSO, DMF and sulfolane, or in ionic liquids. Avoiding aqueous systems leads to better selectivities for HMF purely in terms of the chemical reaction, but for the removal of the solvents, high temperatures are often necessary, at which the thermal decomposition of HMF can occur, which in turn significantly reduces the purity and yield of HMF. In addition, when using water-free systems, the costs for the solvents as well as safety and environmental aspects play a major role. It also proves to be disadvantageous that the hexoses used for HMF synthesis, in particular fructose and/or glucose, have poor solubility in many common organic solvents.

In the two-phase reaction systems, the reaction of hexose to HMF is carried out in an aqueous phase and the resulting HMF is continuously extracted using an organic solvent. The solvent must not be miscible with water and must have a sufficiently high partition coefficient for HMF between the aqueous and organic phases in order to ensure efficient extraction of HMF. Since, in particular, the distribution coefficients for most solvents are not very high, very large amounts of solvent must often be used in such systems. The organic solvent most frequently used in two-phase reaction systems is methyl isobutyl ketone (MIBK), which is optionally used in combination with phase modifiers such as 2-butanol. As already shown for the single-phase anhydrous reaction systems, the subsequent removal of the solvent(s) used proves to be problematic because of the high boiling points of suitable solvents.

EP 0 230 250 Bi discloses a method for the production of 5-hydroxymethylfurfural including a crystalline product using only water as solvent. In the batch method described, saccharides are decomposed in aqueous solution at a temperature of over 100° C. with an acidic catalyst to a mixture of hexoses and HMF and subsequently, the formed HMF is separated over ion exchange columns at a temperature of 35 to 85° C. from byproducts, so that in addition to an HMF fraction, a saccharide fraction can be obtained which is available for another HMF synthesis according to the method described. The batchwise conversion disclosed in this document entails a high fructose conversion and, as a direct result, a high HMF concentration in the reaction solution which, under the prevailing conditions, leads to an increased formation of byproducts and degradation products, whereby the HMF yield is reduced in relation to the converted amount of fructose.

WO 2013/106136 A1 relates to a method for the production of HMF and HMF derivatives from sugar, comprising the recovery of unreacted sugars which are suitable for direct use in ethanol fermentation. Hexose-containing solutions in the aqueous phase are converted into HMF by an acid-catalyzed dehydration reaction, subsequently the unreacted sugars contained in the product mixture are separated from the product mixture by adsorption and/or solvent extraction and these are finally used in aerobic or anaerobic fermentation processes to produce ethanol. It is taught to carry out the acid catalyzed dehydration reaction at a temperature of 175 to 205° C.

WO 2015/113060 A2 discloses the conversion of fructose-containing starting materials to HMF-containing products. By means of the method described, fructose, water, an acid catalyst and at least one other solvent are mixed in a reaction zone and, by choosing suitable reaction parameters, reacted for a period of about 1 to 60 min so that an HMF yield of 80% is not exceeded. When the specified conversion is completed, the reaction components are immediately cooled in order to minimize the formation of undesired byproducts.

WO 2014/158554 discloses a method for the production of HMF or derivatives thereof from solutions containing glucose and/or fructose, wherein the acid-catalyzed dehydration reaction is carried out under oxygen-reduced conditions. This should increase the stability of HMF and prevent possible degradation reactions so that the formation of undesired byproducts is reduced. If necessary, antioxidants are added in order to prevent an auto-oxidation reaction of HMF.

To ensure a cost-effective and effective method for the production of HMF, it is crucial that during the conversion of a fructose-containing starting solution to HMF, the formation of undesired byproducts and the decomposition of HMF formed by the dehydration reaction are avoided as far as possible by choosing suitable reaction conditions and method steps. Furthermore, it makes economic sense if the unconverted fructose is separated from the disruptive byproducts formed during the dehydration reaction and is thus made available in as pure a form as possible for recycling to the continuous production process.

A corresponding method for the cost-effective and effective production of HMF, preferably in a continuous process, is not known from prior art so far.

It is therefore the object of the present invention to overcome the mentioned disadvantages and limitations of the methods known from prior art, in particular to provide a method for converting fructose to HMF in a highly selective manner, in particular with maximum avoidance of byproduct formation and in a cost-effective and effective manner.

The object of the present invention is achieved by the technical teaching of the claims.

In particular, the present invention relates to a method for the production of 5-hydroxymethylfurfural (HMF) comprising the following steps:
a) providing a fructose-containing component and a catalytically active anolyte fraction which has been produced by electrolysis of water,
b) mixing the fructose-containing component and the catalytically active anolyte fraction to obtain a reaction solution,
c) converting the fructose present in the reaction solution to HMF at a temperature of 90° C. to 200° C. to obtain a liquid HMF-containing product mixture and
d) obtaining a liquid HMF-containing product mixture.

According to the invention, a method is accordingly provided which produces 5-hydroxymethylfurfural (HMF) by selective, preferably highly selective, conversion of the fructose of a fructose-containing component. According to the invention, a catalytically active anolyte fraction which has been produced by electrolysis of water is used for converting the fructose. The present invention therefore advantageously provides for a fructose-containing component to be mixed with a catalytically active anolyte fraction and for the fructose present in the reaction solution to be subsequently converted into HMF. The use of a catalytically active anolyte fraction for converting the fructose present in the fructose-containing component to HMF is advantageous in that a significantly higher HMF selectivity is achieved compared to conventional methods for the production of HMF, which use sulfuric acid as a catalyst, while at the same time the formation of byproducts is significantly reduced and fructose is converted at comparable rates. In an advantageous preferred embodiment, fructose conversions≥30% with an acceptable selectivity of more than 80% are possible. In addition, the use of the anolyte fraction also enables a higher carbohydrate concentration in the reaction solution, namely up to 40% dry matter carbohydrate in an advantageous preferred embodiment. According to the invention, the use of the catalytically active anolyte fraction leads to very high HMF selectivities, without the need to use other catalysts in homogeneous or heterogeneous form in an advantageous preferred embodiment. Surprisingly, it could be shown that when using the catalytically active anolyte fraction as a catalyst for the conversion of fructose to HMF, in an advantageous preferred embodiment, there is an inverse relationship between the fructose purity and the HMF selectivity, i.e., the selectivity for HMF increases with a decreasing fructose content in the carbohydrate composition. In addition, the use of the catalytically active anolyte fraction leads to a significantly lower formation of humic substances, in particular insoluble humic substances, which in the usual process lead to technical problems due to caking and incrustations. The use according to the invention of the catalytically active anolyte fraction, which contains oxygen, accordingly leads, in particular, to significantly higher fructose conversions with economically sensible HMF selectivity. This effect is particularly surprising in the light of the aforementioned WO 2014/158554, since in the method described there, in particular, oxygen-reduced conditions and/or the presence of antioxidants lead to increased HMF stability and prevent possible degradation reactions.

In a particularly preferred embodiment, the procedure according to the invention, in particular the implementation of method steps a) to d), enables significantly higher HMF selectivity to be achieved, wherein a reduced byproduct formation, in particular a rehydration of HMF to levulinic acid and formic acid occurs, which is reduced compared to prior art.

In a particularly preferred embodiment, the selectivity for levulinic acid in the method according to the invention, in particular method steps a) to d), is ≤5%, preferably ≤4%, preferably ≤3%, particularly preferably ≤2% (based on the converted fructose content).

In connection with the present invention, a catalytically active anolyte fraction is understood to mean the water fraction obtained in the course of and as a result of an electrolysis of water at the anode. The solution located in the anode space after the electrolysis of the water is used according to the invention as the catalytically active anolyte fraction in the present process. This "catalytically active anolyte fraction" is also referred to here as anolyte, acidic activated water, electrolyzed oxidizing water, acidic electroactivated water or acidic electrochemically activated water.

According to the invention, the catalytically active anolyte fraction is produced in an electrolysis cell in which the cathode is separated from the anode, preferably by a membrane or a diaphragm. After the electrolysis has been carried out, the catalytically active anolyte fraction is removed from the anode compartment of the electrolysis cell and used in the method according to the invention. The water used to produce the catalytically active anolyte fraction is preferably fully demineralized water (DI water), distilled water, drinking water or tap water. However, it can also be provided that the water for the electrolysis comprises a salt. This is preferably selected from the group consisting of LiCl, NaCl, KCl, NaF or other alkali or alkaline earth halides, in particular alkali or alkaline earth chlorides or alkali or alkaline earth fluorides, $NaNO_3$ or other alkali or alkaline earth nitrates, $Na_2SO_4$ or other alkali- or alkaline earth sulfates, sodium citrate or other salts of citric acid, or mixtures thereof. Particularly preferably, the water for the electrolysis has a salt selected from the group consisting of alkali halides, alkaline earth halides, alkali nitrates, alkaline earth nitrates, alkali sulfates, alkaline earth sulfates, citrates, acetates, tartrates, oxalates, glycolates, gluconates and mixtures thereof. The water for the electrolysis particularly preferably contains a salt selected from the group consisting of NaCl, $NaNO_3$, $Na_2SO_4$, LiCl and KCl. In particular, the water preferably contains NaCl. The salt contained in the water for electrolysis is also referred to here as the electrolyte.

According to the invention, the water for the electrolysis is 0.01 to 2.5 wt.-%, preferably 0.05 to 2.2 wt.-%, preferably 0.1 to 2.0 wt.-%, preferably 0.5 to 1.5 wt.-%, particularly preferably 0.1 to 1 wt.-% salt, in particular 0.05 wt.-%, 0.1 wt.-%, 0.18 wt.-%, 0.25 wt.-%, 0.625 wt.-% or 1.0 wt.-% salt (based on the total weight of the water).

By electrolysis of pure water, e.g. fully deionized water or tap water, so without the addition of an electrolyte, that means, a salt, two different solutions are created in the anode and cathode compartment, which are preferably separated from each other by a membrane or a diaphragm. At the anode, electrons and oxygen are formed from hydroxide ions and H$_2$O oxonium ions (H$_3$O$^+$). Small amounts of other reactive species such as ozone (O$_3$) and various radicals such as HO$_2$*, OH* or H$_2$O* can also be formed through secondary reactions on the electrodes. The catalytically active anolyte fraction obtained by the electrolysis of deionized water is therefore characterized in particular by the presence of O$_2$ and oxonium ions (H$_3$O$^+$). Hydroxide ions (OH$^-$) and hydrogen are formed from water at the cathode. Here, too, other reactive species such as peroxide and radicals can be formed through secondary reactions. Since pure water conducts electricity poorly, the reactions mentioned above occur very slowly. In order to accelerate the reactions, water-soluble electrolytes, i.e., salts, are added to increase the conductivity of the water. These electrolytes can then also enter into electrochemical reactions. The electrolysis of water containing NaCl, for example, in an electrolysis cell results in two different solutions in the anode and cathode compartments, which are preferably separated from one another by a membrane or a diaphragm. Negatively charged ions (OH$^-$, Cl$^-$) migrate to the anode and react there to form chlorine (Cl$_2$), oxygen (O$_2$), hypochlorous acid (HClO) and very dilute hydrochloric acid (HCl), so that a solution with a low pH value and a high oxidation-reduction potential is formed. In addition to HClO, chloride can also form HClO$_2$, ClO$_2$, ClO$_3^-$ or also ClO$_4^-$. Positively charged ions (Na$^+$) migrate to the cathode and react to form caustic soda (NaOH) and hydrogen (H$_2$), creating a solution with a high pH value and a low oxidation-reduction potential.

If the catalytically active anolyte fraction was produced from fully demineralized water, it includes, in particular, therefore H$_2$O and H$_3$O$^+$ and optionally dissolved oxygen and a low concentration of OH$^-$. If, in a particularly preferred embodiment, the catalytically active anolyte fraction was produced from at least one salt-containing water, the catalytically active anolyte fraction in particular consists of H$_2$O, H$_3$O$^+$, dissolved oxygen and the anion of the at least one salt. In a preferred embodiment, the catalytically active anolyte fraction therefore has no or only small proportions of the cation of a salt.

In a preferred embodiment, a catalytically active anolyte fraction produced from deionized water has an oxygen content above the saturation concentration. In particular, a catalytically active anolyte fraction produced from deionized water has an oxygen content of 15 to 25 mg/l, preferably 17 to 23 mg/l, preferably 19 to 21 mg/l, particularly preferably 19.5 to 20 mg/l.

In a preferred embodiment, a catalytically active anolyte fraction produced from at least one salt-containing water has an oxygen content above the saturation concentration. In a preferred embodiment, a catalytically active anolyte fraction produced from at least one salt-containing water has an oxygen content of 15 to 30 mg/l, preferably 17 to 27 mg/l, preferably 19 to 25 mg/l, particularly preferably 20 to 22 mg/l.

In preferred embodiments, the catalytically active anolyte fraction used according to the invention has a pH which is above the pH of the homogeneous acids, in particular mineral acids, used as catalysts in known processes. Accordingly, the pH value prevailing in the method according to the invention is also clearly above the pH values prevailing in the acid-catalyzed processes of the prior art. The method according to the invention can advantageously be carried out without the addition of a catalyst in homogeneous or heterogeneous form, in particular without the addition of homogeneous acids or mineral acids. In the method according to the invention, therefore, no further catalytically active component is preferably used, in particular in method steps a) to d), in particular a) to c), apart from the catalytically active anolyte fraction.

According to the invention, the pH of the catalytically active anolyte fraction is 1.5 to 4.5, preferably 2 to 4, preferably 2.5 to 3.5, particularly preferably 2 to 3, in particular 2 to 2.5.

In a particularly preferred embodiment, the catalytically active anolyte fraction is an aqueous solution. According to the invention, a single-phase procedure is preferably provided. A two-phase procedure is preferably excluded. Preferably, no phase separation, in particular no induced phase separation, is provided.

In a particularly preferred embodiment it is provided that in the method according to the invention, in particular in method steps a) to d), in particular a) to c), no organic solvent is used. In particular, in method steps a) to d), in particular a) to c), no organic solvent is used which is miscible with water or immiscible with water.

In particular, method steps a) to d) occur in aqueous solution.

In addition to the catalytically active anolyte fraction, a fructose-containing component is provided in step a) of the method according to the invention. This is preferably a solid fructose-containing component, in particular fructose, or a liquid fructose-containing component, in particular a fructose syrup, a fructose/glucose syrup or a fructose solution, in particular an aqueous fructose solution. The fructose-containing component is therefore also referred to here as the fructose-containing starting solution. According to the invention, the fructose-containing component can also be obtained from sucrose or starch, or glucose obtained from biomass can be isomerized to fructose. The fructose-containing component preferably has a dry matter content (DM) of 40 to 100 wt.-%, preferably 50 to 90 wt.-%, preferably 60 to 85 wt.-% of fructose.

In a preferred embodiment of the present invention, the components provided in step a) are mixed in step b) to obtain a reaction solution with a carbohydrate content of 5 wt.-% to 50 wt.-% (dry matter, hereinafter also DM, carbohydrate in relation to total weight of reaction solution) and converted according to method step c). The carbohydrate content of the reaction solution in step b) is particularly preferably 10 wt.-% to 45 wt.-%, preferably 15 wt.-% to 40 wt.-%, preferably 25 wt.-% to 35 wt.-%, preferably 20 wt.-%, 30 wt.-% or 40 wt.-% (in each case DM carbohydrate in relation to the total weight of the reaction solution).

In a preferred embodiment of the present method, the fructose content of the reaction solution obtained in method step b) is 40 wt.-% to 100 wt.-%, preferably 70 wt.-% to 100 wt.-%, preferably 80 wt.-% to 100 wt.-%, preferably 90 wt.-% to 100 wt.-%, preferably 95 wt.-% to 100 wt.-%, preferably 40 wt.-% to 99 wt.-%, preferably 45 wt.-% to 99 wt.-%, preferably 50 wt.-% to 95 wt.-%, preferably 45 wt.-% to 90 wt.-%, preferably 55 wt.-% to 85 wt.-% (in each case DM fructose in relation to the dry matter of the carbohydrate content, i.e., all the carbohydrates present in the reaction solution).

In a particularly preferred embodiment of the present invention, the components provided in step a) are mixed in step b) to obtain a reaction solution with a carbohydrate content of 5 wt.-% to 50 wt.-%, preferably 10 wt.-% to 45 wt.-%, preferably 15 wt.-% to 40 wt.-%, preferably 25 wt.-% to 35 wt.-%, preferably 20 wt.-%, 30 wt.-% or 40 wt.-%, (each DM carbohydrate in relation to the total weight of the reaction solution) and a fructose content of 40 wt.-% to 100 wt.-%, preferably 70 wt.-% to 100 wt.-%, preferably 80 wt.-% to 100 wt.-%, preferably 90 wt.-% to 100 wt.-%, preferably 95 wt.-% to 100 wt.-%, preferably 40 wt.-% to 99 wt.-%, preferably 45 wt.-% to 99 wt.-%, preferably 50 wt.-% to 95 wt.-%, preferably 45 wt.-% to 90 wt.-%, preferably 55 wt.-% to 85 wt.-% (in each case DM fructose in relation to the dry matter of the carbohydrate content, i.e., all carbohydrates present in the reaction solution) and converted according to method step c).

In a preferred embodiment of the present invention, the ratio of the carbohydrate content (dry matter) of the fructose-containing component to the catalytically active anolyte fraction (total weight) in the reaction solution is 0.01 to 2.5, preferably 0.02 to 2.0, preferably 0.05 to 1.5, preferably 0.1 to 1.0, preferably 0.2 to 0.9, particularly preferably 0.3 to 0.8.

In a preferred embodiment of the present invention, the ratio of the carbohydrate content (dry matter) of the fructose-containing component to the catalytically active anolyte fraction (total weight) in the reaction solution is 0.01 to 2.5, preferably 0.02 to 2.0, preferably 0.05 to 1.5, preferably 0.1 to 1.0, preferably 0.2 to 0.9, particularly preferably 0.3 to 0.8 and the carbohydrate content of the reaction solution is in total 5 wt.-% to 50 wt.-%, preferably 10 wt.-% to 45 wt.-%, preferably 15 wt.-% to 40 wt.-%, preferably 25 wt.-% to 35 wt.-%, preferably 20 wt.-%, 30 wt.-% or 40 wt.-% (in each case DM carbohydrate in relation to the total weight of the reaction solution).

In a preferred embodiment of the present invention, the ratio of the carbohydrate content (dry matter) of the fructose-containing component to the catalytically active anolyte fraction (total weight) in the reaction solution is 0.01 to 2.5, preferably 0.02 to 2.0, preferably 0.05 to 1.5, preferably 0.1 to 1.0, preferably 0.2 to 0.9, particularly preferably 0.3 to 0.8 and the carbohydrate content of the reaction solution is in total 5 wt.-% to 50 wt.-%, preferably 10 wt.-% to 45 wt.-%, preferably 15 wt.-% to 40 wt.-%, preferably 25 wt.-% to 35 wt.-%, preferably 20 wt.-%, 30 wt.-% or 40 wt.-% (in each case DM carbohydrate in relation to the total weight of the reaction solution) containing a fructose content of 40 wt.-% to 100 wt.-%, preferably 70 wt.-% to 100 wt.-%, preferably 80 wt.-% to 100 wt.-%, preferably 90 wt.-% to 100 wt.-%, preferably 95 wt.-% to 100 wt.-%, preferably 40 wt.-% to 99 wt.-%, preferably 45 wt.-% to 99 wt.-%, preferably 50 wt.-% to 95 wt.-%, preferably 45 wt.-% to 90 wt.-%, preferably 55 wt.-% to 85 wt.-% (in each case DM fructose in relation to the dry matter of the carbohydrate content, i.e., all carbohydrates present in the reaction solution).

In a preferred embodiment of the present invention, the ratio of the fructose content (dry matter) of the fructose-containing component to the catalytically active anolyte fraction (total weight) in the reaction solution is 0.01 to 2.5, preferably 0.02 to 2.0, preferably 0.05 to 1.5, preferably 0.1 to 1.0, preferably 0.2 to 0.9, particularly preferably 0.3 to 0.8.

In a preferred embodiment of the present invention, the ratio of the fructose content (dry matter) of the fructose-containing component to the catalytically active anolyte fraction (total weight) in the reaction solution is 0.01 to 2.5, preferably 0.02 to 2.0, preferably 0.05 to 1.5, preferably 0.1 to 1.0, preferably 0.2 to 0.9, particularly preferably 0.3 to 0.8 and the carbohydrate content of the reaction solution is in total 5 wt.-% to 50 wt.-%, preferably 10 wt.-% to 45 wt.-%, preferably 15 wt.-% to 40 wt.-%, preferably 25 wt.-% to 35 wt.-%, preferably 20 wt.-%, 30 wt.-% or 40 wt.-% (in each case DM carbohydrate in relation to the total weight of the reaction solution).

In a preferred embodiment of the present invention, the ratio of the fructose content (dry matter) of the fructose-containing component to the catalytically active anolyte fraction (total weight) in the reaction solution is 0.01 to 2.5, preferably 0.02 to 2.0, preferably 0.05 to 1.5, preferably 0.1 to 1.0, preferably 0.2 to 0.9, particularly preferably 0.3 to 0.8 and the carbohydrate content of the reaction solution is in total 5 wt.-% to 50 wt.-%, preferably 10 wt.-% to 45 wt.-%, preferably 15 wt.-% to 40 wt.-%, preferably 25 wt.-% to 35 wt.-%, preferably 20 wt.-%, 30 wt.-% or 40 wt.-% (in each case DM carbohydrate in relation to the total weight of the reaction solution) containing a fructose content of 40 wt.-% to 100 wt.-%, preferably 70 wt.-% to 100 wt.-%, preferably 80 wt.-% to 100 wt.-%, preferably 90 wt.-% to 100 wt.-%, preferably 95 wt.-% to 100 wt.-%, preferably 40 wt.-% to 99 wt.-%, preferably 45 wt.-% to 99 wt.-%, preferably 50 wt.-% to 95 wt.-%, preferably 45 wt.-% to 90 wt.-%, preferably 55 wt.-% to 85 wt.-% (in each case DM fructose in relation to the dry matter of the carbohydrate content, that means all the carbohydrates present in the reaction solution).

In a preferred embodiment of the present invention, the ratio of the catalytically active anolyte fraction (total weight) to the carbohydrate content (dry matter) of the fructose-containing component in the reaction solution is 0.4 to 100, preferably 0.5 to 50, preferably 0.7 to 20, preferably 1.0 to 10, particularly preferably 1.1 to 5, preferably 1.25 to 3.3.

In a preferred embodiment of the present invention, the ratio of the catalytically active anolyte fraction (total weight) to the fructose content (dry matter) of the fructose-containing component in the reaction solution is 0.4 to 100, preferably 0.5 to 50, preferably 0.7 to 20, preferably 1.0 to 10, particularly preferably 1.1 to 5, preferably 1.25 to 3.3.

According to the invention, the concentration of anions of the catalytically active anolyte fraction in the reaction solution obtained in method step b) is $1 \times 10^{-5}$ to 0.5 mol/l, preferably $1.5 \times 10^{-5}$ to 0.45 mol/l, preferably $1 \times 10^{-4}$ to 0.4 mol/l, preferably $1 \times 10^{-3}$ to 0.35 mol/l, particularly preferably 0.01 to 0.3 mol/l.

In a particularly preferred embodiment, the mixing, i.e., step b) of the method according to the invention, of the components used to prepare the reaction solution, i.e., in particular the fructose-containing component and the catalytically active anolyte fraction, occur in a mixing device and/or a conduit. The mixing device or the conduit and the reactor system in which the conversion, i.e., step c) of the present method occurs, can represent spatially separate structural units that are connected to one another by at least one conduit; they can also represent separate but integral components of a device. The reaction solution is preferably introduced into the reactor system with the aid of a pump, in particular a high pressure pump.

In a preferred embodiment of the present invention, the fructose-containing component provided in step a), the anolyte fraction or both is set to a temperature of 90° C. to 200 C before step b). Preference is therefore given before step b) to at least one, preferably all, of the components provided in step a), i.e., the fructose-containing component and the catalytically active anolyte fraction are preheated separately from one another to a temperature of 90° C. to 200° C., preferably 100° C. to 175° C., preferably 150° C. to 175° C. In a preferred embodiment of the present invention, at least one, preferably all, of the components provided in step a) are preheated to a temperature of 120° C. to 180° C., preferably 130° C. to 180° C., preferably 140° C. to 180° C. before step b). In particular, before step b) at least one, preferably all of the components provided in step a) are preheated separately from one another to a temperature of 160° C., 165° C., 170° C. or 175° C.

In an alternative preferred embodiment of the present invention, the reaction solution obtained in step b) is set to a temperature of 90° C. to 200° C. Preference is therefore given to the reaction solution obtained in step b) by mixing the components provided in step a), preferably after step b) and before step c), to a temperature of 90° C. to 200° C., preferably 100° C. to 175° C., preferably 150° C. to 175° C. The reaction solution obtained in step b), preferably after step b) and before step c), is preferably heated to a temperature of 120° C. to 180° C., preferably 130° C. to 180° C., preferably 140° C. to 180° C. In particular, the reaction solution obtained in step b) is heated to a temperature of 160° C., 165° C., 170° C. or 175° C.

In a particularly preferred embodiment, the subsequent step c) of the present method, i.e., the conversion of the fructose present in the reaction solution to HMF, is carried out at a temperature of 90 to 200° C., in particular 120 to 195° C., in particular 140 to 190° C., in particular 150 to 180° C., in particular 160 to 175° C., in particular 165 to 170° C., in particular 165 to 175° C., in particular 170 to 175° C., in particular 160 to 165° C., in particular 165° C., in particular 170° C., in particular 175° C.

According to the invention, at any point in time, the temperature used to carry out the method according to the invention is, in a preferred embodiment, at most 200° C., preferably at most 175° C., in particular at most 165° C.

In a preferred embodiment of the present invention, the fructose contained in the reaction solution is converted to HMF in step c) in a period of 0.1 to 20 min, in particular 0.1 to 15 min, in particular 8 to 13 min, in particular 4 to 10 min, in particular 8 to 10 min, preferably 0.1 to 8 min, preferably 0.2 to 7 min, preferably 0.5 to 5 min, preferably 1 to 4 min, preferably 5 to 6 min. The fructose is preferably converted to HMF in step c) in a period of at most 10 min, preferably at most 9 min, preferably at most 8 min, preferably at most 7 min, preferably at most 6 min, preferably at most 5 min, preferably at most 4 min.

In a preferred embodiment, the invention provides that a fructose conversion of 1 mol-% to 50 mol-% is achieved in step c). In a preferred embodiment, the fructose is converted to HMF in step c) with a fructose conversion of 1 mol-% to 50 mol-%, preferably 5 mol-% to 40 mol-%, preferably 10 mol-% to 30 mol-%, preferably 15 mol-% to 25 mol-%, preferably 20 mol-% to 25 mol-%. The fructose is preferably converted to HMF in step c) with a fructose conversion of at most 50 mol-%, preferably at most 40 mol-%, preferably at most 30 mol-%, preferably at most 25 mol-%, preferably at most 20 mol-%. According to the invention, this occurs at a temperature of 90° C. to 200° C.

In connection with the present invention, "setting a fructose conversion" means that the reaction parameters used for the conversion of fructose to HMF, in particular the reaction temperature and the reaction time in the reactor, are chosen so that there is only a limited conversion of fructose of a maximum of 50 mol-%, whereby a high HMF selectivity and at the same time a low byproduct formation can be achieved.

It is therefore preferably possible to provide specifically defined fructose conversions within the framework of the given parameters, in particular by using the reaction temperature preferred according to the invention, optionally also the reaction time in a preferred embodiment, for step c). An HMF selectivity which is preferred according to the invention can also be set on the basis of these parameters. In a preferred manner according to the invention, the desired fructose conversion and, optionally, the HMF selectivity can be set by taking a sample during the process, analyzing the sample and then calculating the parameters to be maintained or set to achieve the desired fructose conversion values and the optionally desired HMF selectivity.

In a particularly preferred embodiment, the fructose contained in the fructose-containing component is converted in step c) at a temperature of 90 to 200° C., preferably 150 to 190° C., in particular 160° C., 165° C., 170° C. or 175° C. for a period of 4 to 7 min, preferably 5 to 6 min, in particular 5.6 min. This preferably leads to a fructose conversion of 1 to 50 mol-%.

In a preferred embodiment of the present invention, the method is set so that in step c) an HMF selectivity of 60 mol-% to 100 mol-%, preferably 65 mol-% to 100 mol-%, preferably 70 mol-% 30 to 100 mol-%, preferably 75 mol-% to 100 mol-%, preferably 80 mol-% to 100 mol-%, preferably 85 mol-% to 100 mol-%, preferably 90 mol-% to 100 mol-% is obtained. The HMF selectivity in step c) is preferably at least 60 mol-%, preferably at least 65 mol-%, preferably at least 70 mol-%, preferably at least 75 mol-%, preferably at least 80 mol-%, preferably at least 85 mol-%, preferably at least 90 mol-%, preferably at least 95 mol-%.

In a preferred embodiment of the present invention, the method is set so that in step c) an HMF selectivity of 60 mol-% to 100 mol-%, preferably 65 mol-% to 100 mol-%, preferably 70 mol-% to 100 mol-%, preferably 75 mol-% to 100 mol-%, preferably 80 mol-% to 100 mol-%, preferably 85 mol-% to 100 mol-%, preferably 90 mol-% to 100 mol-%, preferably at least 60 mol-%, preferably at least 65 mol-%, preferably at least 70 mol-%, preferably at least 75 mol-%, preferably at least 80 mol-%, preferably at least 85 mol-%, preferably at least 90 mol-%, preferably at least 95 mol-% and a fructose conversion of 1 mol-% to 50 mol-%, preferably 5 mol-% to 40 mol-%, preferably 10 mol-% to 30 mol-%, preferably 15 mol-% to 25 mol-%, preferably 20 mol-% to 25 mol-%, preferably at most 50 mol-%, preferably at most 40 mol-%, preferably at most 30 mol-%, preferably at most 25 mol-%, preferably at most 20 mol-% is obtained.

In a particularly preferred embodiment of the present invention, the method is set so that in step c) an HMF selectivity of 60 mol-% to 100 mol-%, preferably 65 mol-% to 100 mol-%, preferably 70 mol-% to 100 mol-%, preferably 75 mol-% to 100 mol-%, preferably 80 mol-% to 100 mol-%, preferably 85 mol-% to 100 mol-%, preferably 90 mol-% to 100 mol-%, preferably at least 60 mol-%, preferably at least 65 mol-%, preferably at least 70 mol-%, preferably at least 75 mol-%, preferably at least 80 mol-%, preferably at least 85 mol-%, preferably at least 90 mol-%, preferably at least 95 mol-% and a fructose conversion of 1 mol-% to 50 mol-%, preferably 5 mol-% to 40 mol-%, preferably 10 mol-% to 30 mol-%, preferably 15 mol-% to 25 mol-%, preferably 20 mol-% to 25 mol-%, preferably at most 50 mol-%, preferably at most 40 mol-%, preferably at most 30 mol-%, preferably at most 25 mol-%, preferably at most 20 mol-%, using a temperature of 90 to 200° C., in particular 140 to 190° C., in particular 150 to 180° C., in particular 160 to 175° C., in particular 165 to 170° C., in particular 165 to 175° C., in particular 170 to 175° C., in particular 160 to 165° C., in particular 165° C., in particular 170° C., in particular 175° C. and within a period of 0.1 to 20 min, in particular 0.1 to 15 min, in particular 8 to 13 min, in particular 4 to 10 min, in particular 8 to 10 min, preferably 0.1 to 8 min, preferably 0.2 to 7 min, preferably 0.5 to 5 min, preferably 1 to 4 min, preferably 5 to 6 min is obtained.

In connection with the present invention, the HMF selectivity is related to the content of the converted fructose, wherein contents of other carbohydrates, in particular glucose, are not taken into account.

In a preferred embodiment of the present invention, the HMF yield is 3 to 50 mol-%, preferably 5 to 45 mol-%, preferably 10 to 40 mol-%, preferably 15 to 35 mol-%, particularly preferably 20 to 30 mol-%.

In a preferred embodiment of the present invention, in step c) the pressure for converting the fructose present in the reaction solution to HMF is set such that boiling of the reaction solution and thus the occurrence of vapor bubbles is avoided. The pressure for converting the fructose present in the reaction solution to HMF in the reactor system is preferably 0.1 to 2 MPa, preferably 0.2 to 1.5 MPa, particularly preferably 1 MPa.

According to the invention it is provided that the fructose present in the reaction solution is converted to HMF in step c) by setting various parameters such as temperature, reaction time and/or pressure and a liquid HMF-containing product mixture is obtained in step d). The method is therefore preferably carried out in such a way that by setting the temperature, and preferably also the reaction time, the targeted limited conversion of fructose of 1 mol-% to 50 mol-% occurs, whereby a surprisingly high HMF selectivity, preferably of 60 mol-% to 100 mol-% can be achieved.

In a particularly preferred embodiment, the conversion of fructose present in the reaction solution into HMF and the obtaining of HMF according to method steps c) and d) provides a one-step method according to the invention. In particular, the procedure according to the invention according to method steps c) and d) is preferably not a two-stage procedure.

In a preferred embodiment, the present method further comprises the following step:

e) cooling the liquid HMF product mixture obtained in step d) to a temperature of 20° C. to 80° C., preferably 25° C. to 70° C., preferably 30° C. to 60° C., preferably 30° C. to 55° C., preferably 30° C. to 50° C., preferably 30° C. to 45° C., preferably 30° C. to 40° C., preferably 80° C., preferably 70° C., preferably 60° C., preferably 55° C., preferably 50° C., preferably 45° C., preferably 40° C., preferably 35° C., preferably 30° C. The liquid HMF product mixture in step e) is preferably heated to a temperature of at most 75° C., preferably at most 70° C., preferably at most 60° C., preferably at most 55° C., preferably at most 50° C., preferably at most 45° C., preferably at most 40° C., preferably at most 35° C. According to the invention, this can be done in one or two stages.

In a preferred embodiment of the present invention, the temperature of the liquid HMF product mixture in step e) is set or cooled in a period of 0.1 to 10 min, preferably 0.1 to 9 min, preferably 0.1 to 8 min, preferably 0.2 to 7 min, preferably 0.2 to 6 min, preferably 0.5 to 5 min, preferably 0.5 to 4 min, preferably 0.5 to 3 min. Preferably, the temperature of the product mixture in step e) is set or cooled in at most 10 min, preferably at most 9 min, preferably at most 8 min, preferably at most 7 min, preferably at most 6 min, preferably at most 5 min, preferably at most 4 min, preferably at most 3 min, preferably at most 2 min, preferably at most 1 min, preferably at most 0.5 min.

Thus, the HMF-containing product mixture obtained in step d) is cooled to a temperature of 20° C. to 80° C. after reaching the limited fructose conversion of a maximum of 50 mol-% in step e). This advantageously largely prevents the formation of undesired byproducts and the decomposition of the HMF formed.

The method according to the invention for the production of HMF is preferably carried out in a suitable reactor system. According to the invention, this is preferably a continuous reactor system.

In a particularly preferred embodiment, the continuous reactor system used is designed as a tubular reactor system. Such a continuous reactor system is a reactor system known to the person skilled in the art. In a particularly preferred embodiment, a continuous reactor system, in particular a continuous system, with little backmixing can also be used. In a particularly preferred embodiment, a plug-flow reactor (PFR) can be used as the continuous reactor system. In a preferred embodiment, the continuous reactor system can also be designed as a flow tube, stirred kettle or stirred kettle cascade. In connection with the present invention, a plug-flow reactor (PFR) is understood to mean a so-called ideal flow tube (IR), that means a tubular reactor in which there is a plug flow. A reactor of this type is also distinguished in particular by the fact that there is no mixing, backflow or turbulence of the reaction solution carried out, but rather a uniform flow occurs with material conversion taking place in parallel. The plug-flow reactor ensures, in particular, that each substance fed into the plug-flow reactor, in particular each component fed in, is continuously converted under the same conditions, that means that all components are exposed to the conversion process for the same period of time.

In a preferred embodiment, the present method optionally further comprises the following step:

f) filtration, decolorization and/or purification of the liquid HMF product mixture.

That means, in a further preferred embodiment, the HMF product mixture is filtered, preferably using a suitable filter or a suitable filter system, and the product mixture is decolorized and/or purified, preferably decolorized and/or purified using activated carbon. The product mixture is preferably filtered using a suitable filter or a suitable filter system and the product mixture is decolorized and/or purified, using for example activated carbon, after step e). The product mixture is preferably filtered using a suitable filter or a suitable filter system and the product mixture is decolorized and/or purified, for example using activated carbon, before step g) or h). In a particularly preferred embodiment, after method step e) and/or method step g), the product mixture can preferably be filtered using a suitable filter or a suitable filter system and be decolorized and/or purified in any order, in particular using activated carbon and optionally after step g), another filtration using a suitable filter or a suitable filter system can be carried out in this order. In a particularly preferred embodiment, after step e) and/or method step g), firstly a filtration using a suitable filter or a suitable filter system and subsequently a decolorization and/or purification, in particular using activated carbon and optionally after step g), another filtration using a suitable filter or a suitable filter system in this order is carried out. According to the invention, a sintered metal filter is preferably used for the filtration.

Preferably, by filtering the product mixture over a suitable filter or a suitable filter system and decolorizing and/or purifying it over, for example, activated carbon, undesired byproducts, in particular soluble and insoluble humic substances, are removed from the product mixture.

In a preferred embodiment of the present invention, the product mixture obtained in step e) or optionally step f) has a dry matter content of 5 to 50 wt.-%, preferably 10 to 40 wt.-%, preferably at least 5 wt.-%, preferably at least 10 wt.-%, preferably at most 50 wt.-%, preferably at most 40 wt.-%.

If the dry matter content of the product mixture obtained in step e) or, optionally, f) is too low, the invention can provide that the present method optionally further comprises the following step:

g) setting the liquid HMF product mixture to a dry matter content of 20 to 70 wt.-%, preferably 25 to 60 wt.-%, preferably 25 to 50 wt.-%, preferably 30 to 45 wt.-%, preferably 30 to 40 wt.-%.

In a further preferred embodiment, the product mixture obtained in step e) or optionally f) is reduced to a dry matter content of 20 to 70 wt.-%, preferably at least 20 wt.-%, preferably at least 30 wt.-%, preferably at least 40 wt.-%, preferably at least 50 wt.-%, preferably at most 70 wt.-%, preferably at most 60 wt.-%, preferably at most 50 wt.-%.

In a preferred embodiment, the present method further comprises the following steps:

h) purification of the liquid HMF product mixture by means of chromatography, ultra- and/or nanofiltration, extraction with a suitable extractant, adsorption on a suitable material and subsequent targeted desorption and/or electrodialysis to separate at least one HMF fraction, and i) obtaining at least one HMF fraction.

That means, at least one HMF fraction is preferably separated from the liquid HMF-containing product mixture by using at least one of the above-mentioned purification processes, so that only other components contained in the product mixture such as unreacted fructose, glucose or byproducts such as organic acids and humins remain. It can also be provided according to the invention to use a combination of at least two or more of the purification processes mentioned for the separation of at least one HMF fraction and/or optionally other fractions containing one or more other components of the product mixture.

In an alternative preferred embodiment, the present method further comprises the following steps:

h) purification of the liquid HMF product mixture by means of chromatography, ultra- and/or nanofiltration, extraction with a suitable extractant, adsorption on a suitable material and subsequent targeted desorption and/or electrodialysis to separate at least one fraction selected from the group consisting of an HMF fraction, a glucose fraction, a fructose fraction and an organic acid fraction, and i) obtaining at least one fraction selected from the group consisting of an HMF fraction, a glucose fraction, a fructose fraction and an organic acid fraction.

It can further be provided that at least one of the fractions obtained in step i) is further processed using a purification process selected from the group consisting of chromatography, ultra- and/or nanofiltration, extraction with a suitable extractant, adsorption on a suitable material and subsequent targeted desorption and/or electrodialysis.

One of the purification processes provided in the method according to the invention is ultra- and/or nanofiltration. Suitable membranes can be used to firstly concentrate the liquid HMF-containing product mixture, but also to remove soluble and/or insoluble humins or, in the case of nanofiltration, to separate HMF and/or organic acids from the product mixture. A concentrated product mixture, a product mixture freed from soluble and/or insoluble humic substances, an HMF fraction and a product mixture freed from HMF, an HMF fraction and/or an organic acids fraction and a product mixture freed from HMF and/or organic acids, or a glucose and/or fructose fraction and a product mixture freed from humins and/or glucose and/or fructose can preferably be obtained by ultra and/or nano filtration.

Another purification process provided in the method according to the invention is extraction with a suitable extraction agent. To extract HMF from the HMF-containing product mixture, a solvent is preferably used which is immiscible or hardly miscible with water and which has a sufficiently high affinity for HMF. Ideally, the boiling point of the organic solvent is preferably relatively low and the density difference between water and the solvent is sufficiently high so that phase separation can be achieved. Suitable solvents are preferably methyl isobutyl ketone, ethyl acetate, methyl ethyl ketone, butanol, diethyl ether, methyl butyl ether, isoamyl alcohol, methyl tetrahydrofuran or the like. After the extraction step, an aqueous product mixture that contains unreacted fructose and glucose remains and an organic phase that contains HMF and possibly organic acids is obtained.

Another purification process provided in the method according to the invention is the adsorption onto a suitable material and the subsequent desorption. In principle, HMF can be adsorbed on any material that preferentially adsorbs HMF from hexose-containing solutions. Preferred materials are polymer-based resins such as divinylbenzene-styrene copolymers, adsorber resins, activated carbon, zeolites, aluminum oxides, non-functionalized resins or cation exchange resins. The product mixture obtained in step e), f) or g) is preferably brought into contact continuously with the HMF-adsorbing material, but at most until the material is exhausted. The adsorbed HMF is then desorbed with a suitable desorbent such as water or polar organic solvents such as alcohols, ethyl acetate, THF or the like. HMF can then be obtained from the organic solvent by suitable processes.

Another purification process provided in the method according to the invention is electrodialysis. This is an electrochemically driven membrane process in which ion exchange membranes are used in combination with an electrical potential difference to separate ionic species from uncharged species or impurities in the solution. In the case of the present method, electrodialysis can be used to free the product mixture from inorganic and/or organic cations and anions such as electrolytes from the anolyte fraction, levulinic and formic acid as byproducts.

Another purification process provided in the method according to the invention is chromatography. This is explained in more detail below.

All of the above-mentioned purification processes can be used individually or in combination with one another.

In step h), HMF contained in the product mixture is particularly preferably separated from the other components of the product mixture using a chromatographic method, in particular by means of chromatography on ion exchange resins, in particular cation exchange resins, in particular by means of single or multi-stage chromatography on ion exchange resins, in particular cation exchange resins.

In a particularly preferred embodiment of the present invention, the chromatography, in particular chromatography on ion exchange resins, in particular chromatography on cation exchange resins, is ion exchange chromatography, in particular cation exchange chromatography.

In a preferred embodiment of the present invention, the liquid HMF product mixture is separated in step h) by means of chromatography into at least four fractions, comprising an HMF fraction, a glucose fraction, a fructose fraction and an organic acid fraction, and in step i) at least one HMF fraction, a glucose fraction, a fructose fraction and an organic acid fraction are obtained.

The purification of the product mixture obtained in step e), optionally f) or optionally g) according to step h) is particularly preferably carried out continuously by means of chromatography. Continuous chromatography is preferably also understood to mean simulated chromatography by counterflow, such as, for example, Simulated Moving Bed Chromatography (SMB).

Continuous chromatography processes are well known to the person skilled in the art. For example, US 2011/0137084 A1 shows how the SMB method works. Further suitable chromatography methods are disclosed in A. Rajendran et al.; J. Chromatogr. A 1216 (2009), pages 709-738.

Simulated Moving Bed (SMB) systems or further developments of the SMB system, such as Sequential SMB (SSMB), Intermittent/Improved SMB (ISMB) or New MCI (NMCI), advantageously allow the separation and recovery of the four fractions described in continuous operation.

In a preferred embodiment of the present invention, the chromatography, in particular chromatography on ion exchange resins, in step h) is a Simulated Moving Bed method (SMB), a Sequential Simulated Moving Bed method (SSMB) or an Improved Simulated Moving Bed method or Intermittent Simulated Moving Bed method (ISMB). Preferably, chromatography, in particular chromatography on ion exchange resins, is in step h) a Simulated Moving Bed method (SMB), a Sequential Simulated Moving bed method (SSMB), an Improved Simulated Moving Bed method (ISMB) or a New MCI method (NMCI). It is advantageously possible to carry out the purification of the product mixture obtained in step e), f) or g) for the separation of an HMF fraction, a glucose fraction, a fructose fraction and an organic acid fraction in a continuous procedure through the use of a Simulated Moving Bed method (SMB), a Sequential Simulated Moving Bed method (SSMB), an Improved Simulated Moving Bed method (ISMB) or a New MCI method (NMCI) in step h).

In a preferred embodiment of the present invention, the chromatography, in particular chromatography on ion exchange resins, in particular on cation exchange resins in step h) is a one-step process. The chromatography, in particular chromatography on ion exchange resins, in particular on cation exchange resins in step h) is preferably a multi-stage process, preferably a two-stage process.

The chromatography, in particular chromatography on ion exchange resins, in particular on cation exchange resins, in step h) preferably comprises several stages, preferably at least two stages, preferably at least three stages, preferably two stages, preferably three stages.

In a preferred embodiment of the present invention in step h) in a first stage of the chromatography the separation of at least one fraction, preferably exactly one fraction, in particular an HMF fraction or a glucose fraction, preferably of at least two fractions, preferably of exactly two fractions, preferably of exactly three fractions occurs.

In a further preferred embodiment of the present invention in step h) in a second stage of the chromatography the separation of at least one fraction, preferably exactly one fraction, preferably at least two fractions, preferably exactly two fractions, preferably exactly three fractions, in particular a glucose fraction, a fructose fraction and an organic acid fraction or an HMF fraction, a fructose fraction and an organic acid fraction occurs.

In a preferred embodiment of the present invention, the first stage of the chromatography in step h) is a chromatography method selected from the group consisting of Simulated Moving Bed method (SMB), Sequential Simulated Moving Bed method (SSMB), Improved Simulated Moving Bed method (ISMB) and New MCI method (NMCI).

The first stage of the chromatography in step h) is preferably an Improved Simulated Moving Bed method (ISMB). Preferably, in step h) in a first stage the separation of at least one fraction, preferably exactly one fraction, in particular an HMF fraction or an organic acid fraction occurs by means of a chromatography process selected from the group consisting of the Simulated Moving Bed method (SMB), Sequential Simulated Moving Bed method (SSMB), Improved Simulated Moving Bed method (ISMB) and New MCI method (NMCI), preferably by means of an Improved Simulated Moving Bed method (ISMB).

In a preferred embodiment of the present invention, the second stage of the chromatography in step h) is a chromatography method selected from the group consisting of Simulated Moving Bed method (SMB), Sequential Simulated Moving Bed method (SSMB), Improved Simulated Moving Bed method (ISMB) and New MCI method (NMCI).

The first stage of the chromatography in step h) is preferably a New MCI method (NMCI). Preferably, in step h) in a second stage, the separation of at least one fraction, preferably exactly one fraction, preferably at least two fractions, preferably exactly two fractions, preferably at least three fractions, preferably exactly three fractions, in particular a glucose fraction, a fructose fraction and an organic acid fraction or an HMF fraction, a fructose fraction and an organic acid fraction occurs, by means of a chromatographic method selected from the group consisting of Simulated Moving Bed method (SMB), Sequential Simulated Moving Bed method (SSMB), Improved Simulated Moving Bed method (ISMB) and New MCI method (NMCI), preferably using a New MCI method (NMCI).

In particular, at least two-stage chromatographic separation is preferred, in which the separation of the HMF fraction occurs in the first stage. Alternatively, in the first stage, the separation of the glucose fraction may occur. Preferably, the first stage of the at least two-stage chromatographic separation is a Moving Bed method (ISMB). Preferably, the second stage of the at least two-stage chromatographic separation is a New MCI method (NMCI).

A two-stage chromatographic separation in which the separation of the HMF fraction occurs in the first stage is particularly preferred. Alternatively, in the first stage, the separation of the glucose fraction may occur. Preferably, the first stage of the two-stage chromatographic separation is a Moving Bed method (ISMB). Preferably, the second stage of the two-stage chromatographic separation is a New MCI method (NMCI). Preferably, the organic acid fraction, the fructose fraction and the glucose fraction are preferably separated from one another in the second stage of the two-stage chromatographic separation. Alternatively, in the second stage of the two-stage chromatographic separation, the organic acid fraction, the fructose fraction and the HMF fraction are separated from one another.

In a preferred embodiment of the present invention, chromatography, in particular chromatography on ion exchange resins in step h) is a chromatography on cation exchange resins.

In a preferred embodiment of the present invention, chromatography, in particular chromatography on ion exchange resins, is carried out in step h) using a cation exchange resin in $H^+$ form.

In a preferred embodiment, the chromatography, in particular chromatography on ion exchange resins, is carried out in step h) at a temperature of 40° C. to 80° C., preferably 40° C. to 70° C., preferably 40° C. to 60° C., preferably 50° C. to 80° C., preferably 50° C. to 70° C., preferably 50° C. to 60° C., preferably 60° C. to 80° C., preferably 60° C. to 70° C.

The fructose fraction optionally obtained in step i) is preferably continuously recycled to method step a). The fructose fraction optionally obtained in step i) is advantageously largely, preferably completely, freed from levulinic acid formed. In a further preferred embodiment, the fructose fraction obtained in step i) is advantageously largely, preferably completely, freed from levulinic and formic acid formed.

In a particularly preferred embodiment, the fructose fraction optionally obtained in step i), optionally after concentration, is continuously and preferably completely recycled to step a). In a further preferred embodiment, the fructose fraction obtained in step i) is continuously, optionally after concentration, at least partially recycled in step a), in particular to at least 70%, preferably to at least 80%, preferably to at least 90%, preferably to at least 95%, preferably to at least 98%, preferably to at least 99%, (in each case wt.-% of the recycled fructose fraction in relation to the fructose fraction obtained in step i)).

According to the invention, a "recycled fructose fraction" is understood to mean an aqueous fraction of unconverted fructose that may be obtained after the purification carried out according to the method according to the invention, i.e., step h), which is largely, preferably completely, free from byproducts formed during fructose conversion, in particular levulin and formic acid and humic substances. The resulting aqueous fraction of unreacted fructose is so pure that, in a preferred embodiment, it is recycled directly to method step a), optionally after concentration, that means, without further purification, and after mixing with the fructose-containing component and the catalytically active anolyte fraction, that means step b), is available for a further conversion to HMF in step c). Step a) of the method according to the invention therefore particularly preferably provides a fructose-containing component, a catalytically active anolyte fraction and a recycled fructose fraction, which are mixed in step b) to obtain a reaction solution. Since in this preferred embodiment there is initially no recycled fructose fraction available when the method according to the invention is initiated, a correspondingly larger amount of the fructose-containing component is preferably used instead in this case.

In step i) of the method according to the invention, i.e., after the purification has been carried out, a glucose fraction, a fructose fraction and an organic acid fraction, in particular in isolated form, are optionally obtained in addition to the HMF fraction. Advantageously, the individual fractions obtained via the purification processes used have such high purities that they can be used directly in various subsequent processes, optionally after concentration, that means without further purification.

According to the invention, the optionally obtained fructose fraction is preferably largely free, in particular completely free, of levulinic acid formed. According to the invention, the fructose fraction obtained is preferably largely free, in particular completely free from organic acids formed, in particular levulinic and formic acid.

Levulinic acid disadvantageously favors the formation of humic substances during HMF synthesis. Thus, an increased content of levulinic acid in the reaction solution caused by the fructose fraction recycled according to a preferred embodiment would lead to an increased formation of humic substances from HMF and carbohydrates and thus significantly reduce the economic efficiency of the method. The fructose fraction optionally obtained in step i) in the method according to the invention, has, however, advantageously such a high purity, is in particular free from levulinic acid formed, particularly preferably free from levulinic and formic acid, that in a preferred embodiment it can be recycled directly to the process, in particular to step a) for further conversion, optionally after concentration, in particular without purification steps. In particular, the limited conversion of fructose provided by the method according to the invention and the associated reduced formation of byproducts and degradation products, in particular levulinic and formic acid and humic substances, and in a preferred embodiment, the recycling of a fraction separated from the product mixture of unconverted fructose leads to a high HMF selectivity and a high HMF yield.

Surprisingly, when the method according to the invention is carried out, there is an inverse relationship between the fructose purity and HMF selectivity, that means the selectivity for HMF increases as the fructose content in the reaction solution decreases.

In a particularly preferred embodiment, the method according to the invention consists of method steps a), b), c) and d), in particular no further method steps are carried out between these method steps.

In a particularly preferred embodiment of the present invention, the method according to the invention comprises method steps a), b), c) and d), wherein no further method steps are carried out between method steps a), b), c) and d), but optionally after method step d) is carried out, further method steps are carried out.

According to the invention, the present method comprises steps a) to d), preferably a) to e), preferably a) to f), preferably a) to g), preferably a) to h), in particular a) to i). According to the invention, the present method particularly preferably comprises steps a), b), c), d), e), f), g), h) and i). However, it can also be provided that the present method includes steps a), b), c), d), e), h) and i) or a), b), c), d), e), f), h) and i) or a), b), c), d), e), g) h) and i). In a particularly preferred embodiment, the present method consists of method steps a) to d), preferably a) to e), preferably a) to f), preferably a) to g), preferably a) to h), in particular a) to i). In a particularly preferred embodiment, the present method consists of method steps a), b), c), d), e), h) and i) or a), b), c), d), e), f), h) and i) or a), b), c), d), e), g) h) and i). In a preferred embodiment, the method is carried out in the order of method steps a), b), c), d), e), f), g), h) and i). However, it can also be provided that the present method is carried out in the order of method steps a), b), c), d), e), h) and i) or a), b), c), d), e), f), h) and i) or a), b), c), d), e), g) h) and i).

According to the invention, in the method for the production of 5-hydroxymethylfurfural according to steps a) to i), the conversion of fructose present in the reaction mixture to HMF in a continuous reactor system and the subsequent purification of the product mixture obtained for the separation of at least four fractions occurs continuously, that means with constant supply of starting materials and removal of products.

A continuous process according to the invention is preferably understood to mean a process in which not only the reactor system is continuous, but also the purification of the product mixture.

The present invention enables the provision of methods for the production of HMF and/or formic acid and/or levulinic acid, in particular for the simultaneous production from a starting material, namely a fructose-containing component and optionally a recycled fructose fraction.

In a preferred embodiment, the method according to the invention for the production of HMF is therefore also a method for the production of HMF and formic acid and levulinic acid, which comprises steps a) to i) which is used for the targeted production of three products of interest.

In a preferred embodiment, the method according to the invention for the production of HMF is therefore also a method for the production of HMF and formic acid, which comprises steps a) to i) and is used for the production of two valuable substances of interest.

In a preferred embodiment, the method according to the invention for the production of HMF is therefore also a method for the production of HMF and levulinic acid, which comprises steps a) to i) and is used for the production of two valuable substances of interest.

According to the invention, the glucose fraction obtained in step i) comprises at least 20 wt.-% of the glucose contained in the product mixture (in each case DM based on the product mixture).

In a further preferred embodiment of the present invention, the glucose fraction optionally obtained in step i) has a sufficiently high purity, is in particular free from fermentation inhibitors, so that it can be used directly, optionally after concentration, both as a feed (feed material) in fermentative processes, in particular for the production of ethanol, in particular glucose fermentation to ethanol, and as a starting material in chemical processes, in particular the oxidation of glucose to gluconic acid.

In a further preferred embodiment, the glucose fraction optionally obtained in step i) is used for ethanol production, in particular glucose fermentation to form ethanol, in particular for bio-ethanol production, and/or for gluconic acid production.

The present invention therefore also provides a method for the production of a feed for fermentative processes, in particular for the production of ethanol, in particular glucose fermentation to ethanol, or for the production of a starting material, that means an educt, in chemical processes, in particular for the production of gluconic acid, in the context of which a process of the present invention is carried out with method steps a) to i) while obtaining a glucose fraction which can be used as feed or starting material.

In a particularly preferred embodiment, a method for ethanol production, in particular the fermentation of glucose to ethanol, is provided, in the context of which the method according to the invention, in particular method steps a) to i), in particular for obtaining a glucose fraction, are carried out, wherein the glucose fraction obtained is used for the production of ethanol, in particular the fermentation of glucose to ethanol, in particular for the production of bio-ethanol. In a further preferred embodiment, the glucose fraction optionally obtained in step i) is used to obtain gluconic acid, optionally after concentration.

In a particularly preferred embodiment, a method for the production of gluconic acid is provided, which comprises the method according to the invention, in particular method steps a) to i), in particular for obtaining a glucose fraction that is used to obtain glucose and to subsequently oxidize glucose to gluconic acid.

In a preferred embodiment of the present invention, the organic acid fraction optionally obtained in step i) is used to isolate levulinic and formic acid. In a further preferred embodiment, the organic acid fraction obtained in step i) is used to isolate levulinic acid. In a further preferred embodiment, the organic acid fraction obtained in step i) is used to isolate formic acid.

The present invention therefore also relates to a method for the production of levulinic acid, formic acid or levulinic acid and formic acid, wherein a method comprising steps a) to i) of the present invention is carried out and levulinic acid, formic acid or levulinic acid and formic acid are obtained in one step i).

In a further preferred embodiment of the present invention, the HMF fraction obtained in step i) is oxidized directly in an additional step to 2,5-furandicarboxylic acid (FDCA), optionally after concentration, that means, without the need for work-intensive further purification.

The present invention therefore also relates to a method for the production of FDCA, comprising steps a) to i) of the present invention, wherein the HMF fraction obtained in step i) is oxidized to FDCA, preferably directly, optionally after concentration, and without the need for work-intensive further purification.

According to the invention, the glucose fraction optionally obtained contains 0.8 wt.-% to 100 wt.-% glucose, 0 wt.-% to 99.2 wt.-% fructose, at most 2 wt.-%, preferably at most 1 wt.-%.-%, preferably at most 0.5 wt.-%, preferably at most 0.1 wt.-%, levulinic and formic acid and at most 10 wt.-%, preferably at most 5 wt.-%, preferably at most 2 wt.-%, more preferably at most 1 wt.-%, preferably at most 0.5 wt.-%, preferably at most 0.1 wt.-%, HMF (in each case DM, based on the total of the components analyzed (glucose, fructose, levulinic acid, formic acid, HMF, difructose anhydrides (DFA))). According to the invention, the glucose fraction preferably contains at most 10 wt.-%, more preferably at most 5 wt.-% of HMF.

The fructose fraction optionally obtained in step i) according to the invention contains at least 70 wt.-%, preferably at least 80 wt.-%, of the fructose contained in the product mixture (in each case DM based on the product mixture).

According to the invention, the optionally obtained fructose fraction contains 0 wt.-% to 60 wt.-% glucose, 40 wt.-% to 100 wt.-% fructose, at most 2 wt.-%, preferably at most 1 wt.-%, preferably at most 0.5 wt.-%, preferably at most 0.1 wt.-%, levulinic acid, at most 2 wt.-%, preferably at most 1.5 wt.-%, preferably at most 1 wt.-%, preferably at most 0.5 wt.-%, preferably at most 0.25 wt.-%, preferably at most 0.1 wt.-%, formic acid and at most 2 wt.-%, preferably at most 1.5 wt.-%, preferably at most 1 wt.-%, preferably at most 0.8 wt.-%, preferably at most 0.6 wt.-%, preferably at most 0.4 wt.-%, preferably at most 0.2 wt.-%, preferably at most 0.1 wt.-%, HMF (in each case DM, based on the total of the components analyzed (glucose, fructose, levulinic acid, formic acid, HMF, difructose anhydrides (DFA)). According to the invention, the fructose fraction preferably contains at most 2 wt.-% HMF. According to the invention, the fructose fraction preferably contains at most 2 wt.-% levulinic acid. In a particularly preferred embodiment, the ratio of fructose to glucose in the fructose fraction is not less than in the fructose-containing component provided in step a).

According to the invention, the organic acid fraction optionally obtained in step i) contains at least 60 wt.-%, preferably at least 65 wt.-%, preferably at least 70 wt.-%, preferably at least 80 wt.-%, preferably at least 90 wt.-%, preferably at least 95 wt.-%, preferably at least 98 wt.-%, preferably at least 99 wt.-%, preferably at least 99.5 wt.-%, preferably at least 99.8 wt.-%, preferably 100 wt.-%.-% of the levulinic and formic acid contained in the product mixture (in each case DM, based on the product mixture).

According to the invention, the organic acid fraction optionally obtained contains 50 wt.-% to 100 wt.-%, preferably 60 wt.-% to 100 wt.-%, preferably, more preferably 65 wt.-% to 100 wt.-%, preferably 70 wt.-% to 100 wt.-%, preferably 80 wt.-% to 100 wt.-%, preferably 90 wt.-% to 100 wt.-%, preferably 95 wt.-% to 100 wt.-%, preferably 98 wt.-% to 100 wt.-%, preferably 99 wt.-% to 100 wt.-%, preferably 99.5 wt.-% to 100 wt.-%, preferably 99.7 wt.-% to 100 wt.-% of levulinic and formic acid (in each case DM, based on the total of the components analyzed (glucose, fructose, levulinic acid, formic acid, HMF, difructose anhydrides (DFA)). According to the invention, the organic acid fraction preferably contains at least 50 wt.-% of levulinic acid, more preferably at least 60 wt.-% of levulinic acid, more preferably at least 70 wt.-% of levulinic acid.

According to the invention, the HMF fraction obtained in step i) contains at least 70 wt.-%, preferably at least 80 wt.-%, more preferably at least 90 wt.-%, preferably at least 98 wt.-%, preferably at least 99 wt.-%, preferably at least 99.5 wt.-%, preferably at least 99.8 wt.-%, preferably 100 wt.-% of HMF contained in the product mixture (in each case DM, based on the product mixture).

According to the invention, the HMF fraction contains 80 wt.-% to 100 wt.-%, preferably 85 wt.-% to 100 wt.-%, preferably 90 wt.-% to 100 wt.-%, preferably 95 wt.-% to 100 wt.-%, preferably 98 wt.-% to 100 wt.-%, preferably 99 wt.-% to 100 wt.-%, preferably 99.5 wt.-% to 100 wt.-%, preferably 99.7 wt.-% to 100 wt.-% HMF and at most 16 wt.-%, preferably at most 14 wt.-%, preferably at most 12 wt.-%, preferably at most 10 wt.-%, preferably at most 8 wt.-%, preferably at most 6 wt.-%, preferably at most 4 wt.-%, preferably at most 2 wt.-%, preferably at most 1 wt.-%, levulinic and formic acid, at most 2 wt.-%, preferably at most 1 wt.-%, preferably at most 0.8 wt.-%, preferably at most 0.6 wt.-%, preferably at most 0.4 wt.-%, preferably at most 0.2 wt.-%, preferably at most 0.1 wt.-% glucose and at most 2 wt.-%, preferably at most 1 wt.-%, preferably at most 0.8 wt.-%, preferably at most 0.6 wt.-%, preferably at most 0.4 wt.-%, preferably at most 0.2 wt.-%, preferably at most 0.1 wt.-% fructose (in each case DM, based on the total of the components analyzed (glucose, fructose, levulinic acid, formic acid, HMF, difructose anhydrides (DFA)).

In a preferred embodiment, no organic solvents, in particular no ionic liquids, are used in the method according to the invention, in particular during steps a) to g), optionally a) to i).

In a preferred embodiment, the method according to the invention, in particular during steps a) to i), is not carried out under oxygen-reduced conditions.

In connection with the present invention, the term "and/or" is understood to mean that all members of a group which are connected by the term "and/or" are disclosed both as alternatives to one another and also cumulatively to one another in any combination. For the expression "A, B and/or C" this means that the following disclosure content is to be understood under this expression: A or B or C or (A and B) or (A and C) or (B and C) or (A and B and C).

In connection with the present invention, the term "comprehensive" is understood to mean that in addition to the elements explicitly covered by the term, further elements that are not explicitly mentioned can be added. In connection with the present invention, these terms are also understood to mean that only the explicitly mentioned elements are included and no further elements are present. In this particular embodiment, the meaning of the term "comprising" is synonymous with the term "consisting of." In addition, the term "comprehensive" also includes entities that, in addition to the explicitly named elements, also contain other elements that are not named, but which are functionally and qualitatively subordinate. In this embodiment, the term "comprising" is synonymous with the term "consisting substantially of."

Further preferred embodiments are particularly found in the dependent claims.

The invention is explained in more detail with reference to the following exemplary embodiments and the associated figures.

The figures show:

EXAMPLES

Figure 1:
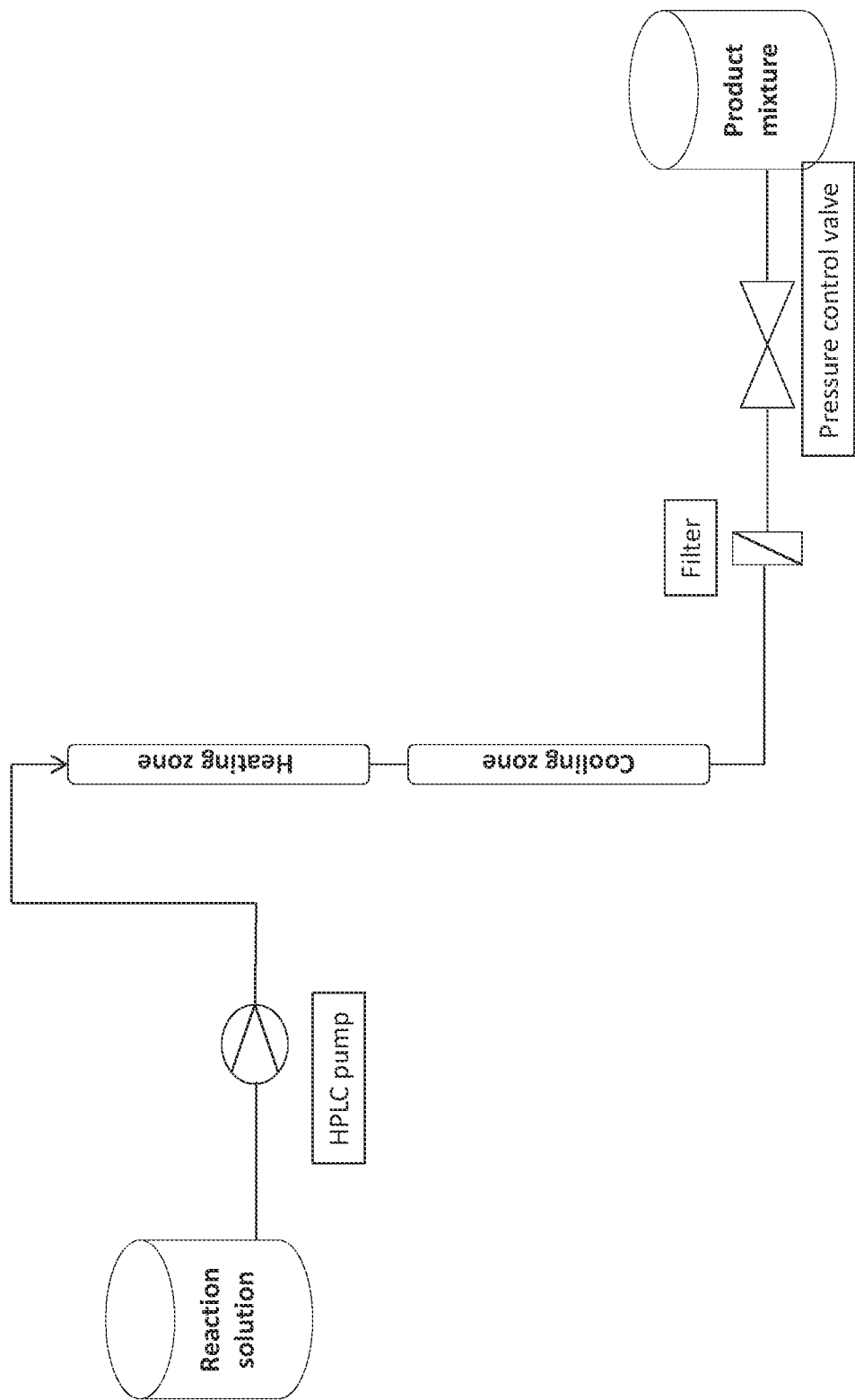
FIG. 1 is a schematic representation of the reactor system used according to the invention.
Figure 2:
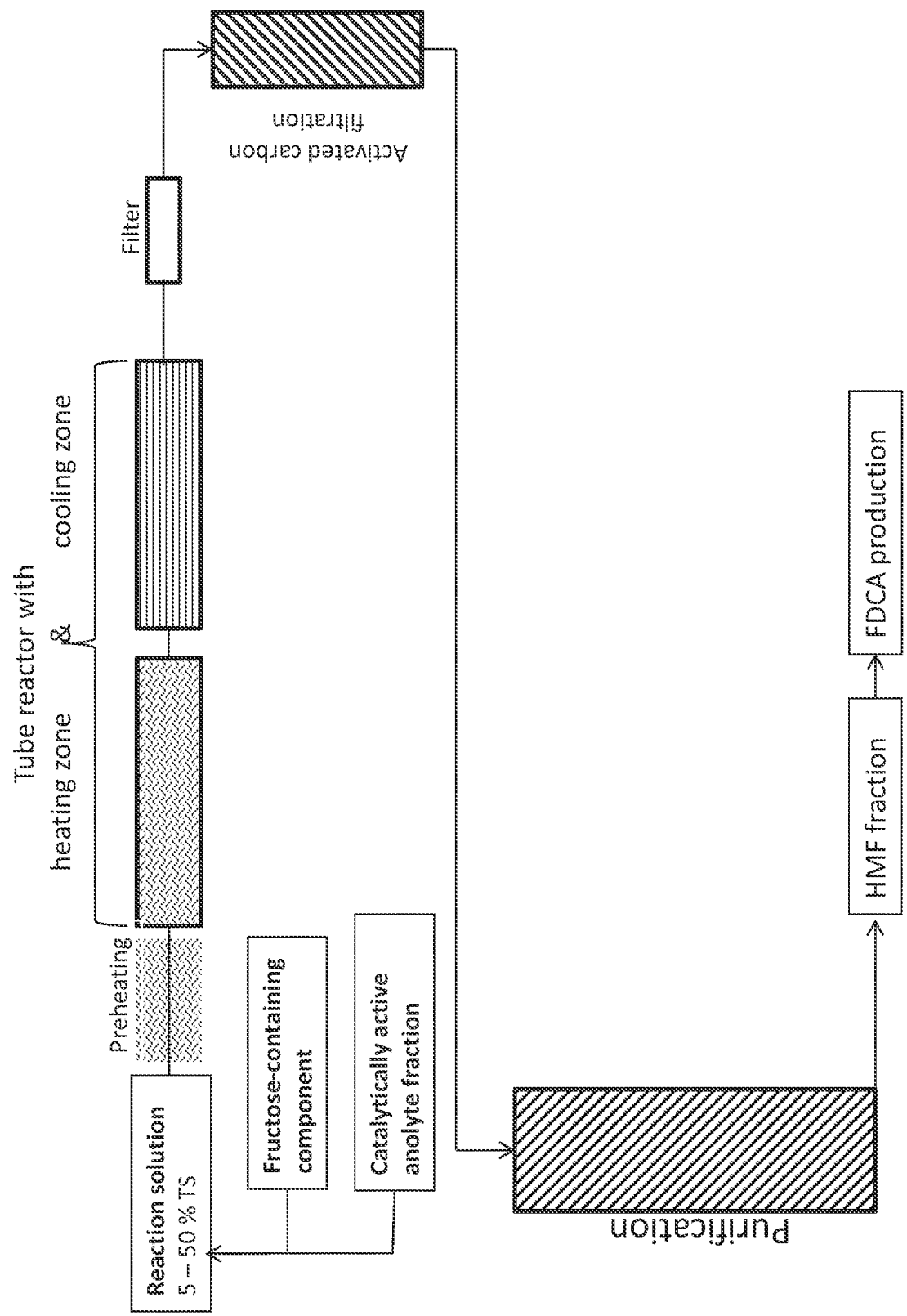
FIG. 2 is a schematic representation of the method according to the invention, wherein the components provided in step a) are initially mixed in step b) and the reaction solution obtained is subsequently heated and an HMF fraction is obtained after the purification step h) (step i)).
Figure 3:
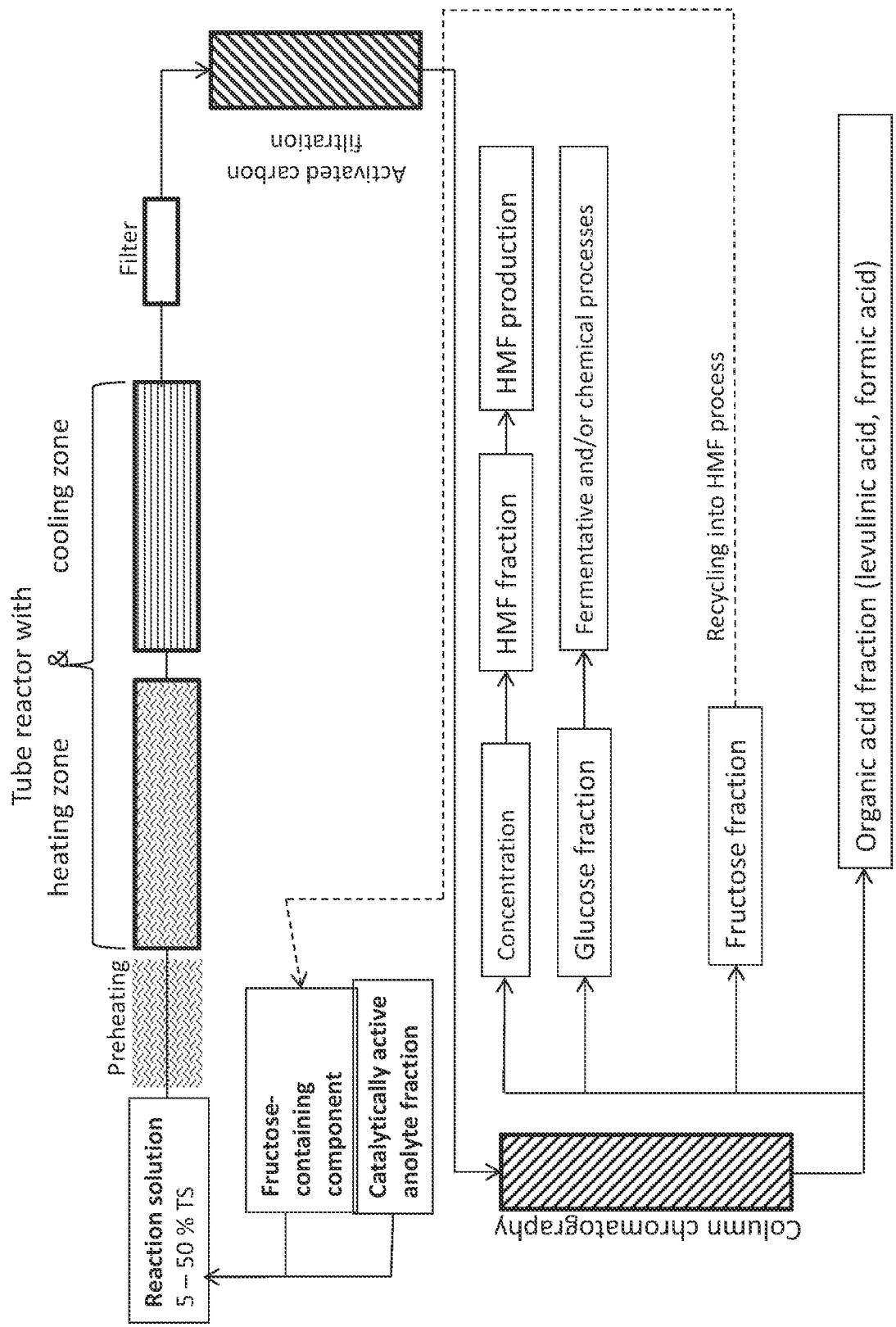
FIG. 3 is a schematic representation of the method according to the invention analogous to FIG. 2, wherein in step h) a column chromatographic separation is carried out and an HMF fraction, a glucose fraction, a fructose fraction and an organic acid fraction is obtained (step i)).
Figure 4:
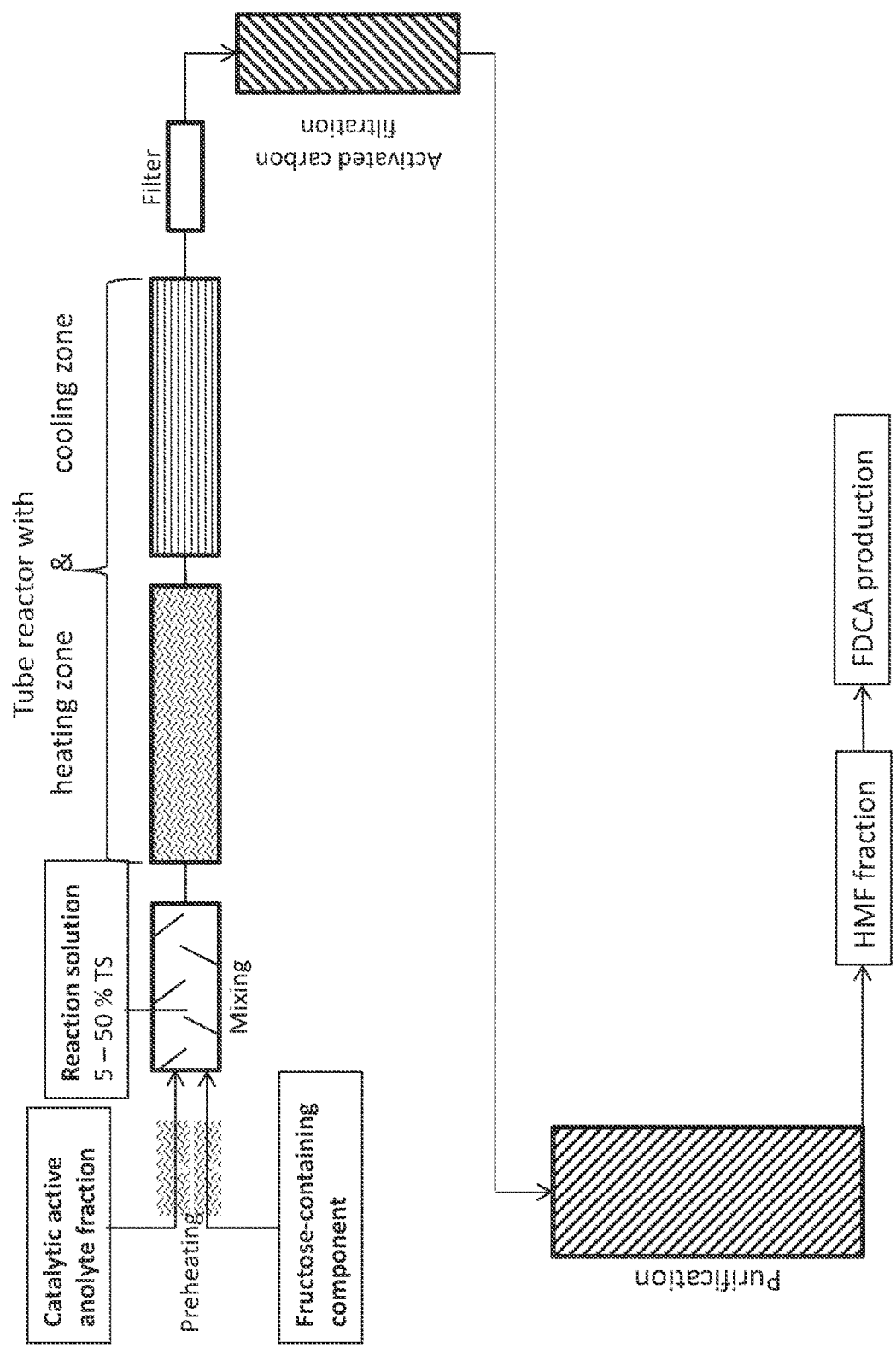
FIG. 4 is a schematic representation of the method according to the invention, wherein the components provided in step a) are heated separately from one another and are only subsequently mixed in step b) to obtain a reaction solution, and wherein an HMF fraction is obtained after purification step h) (step i)).
Figure 5:
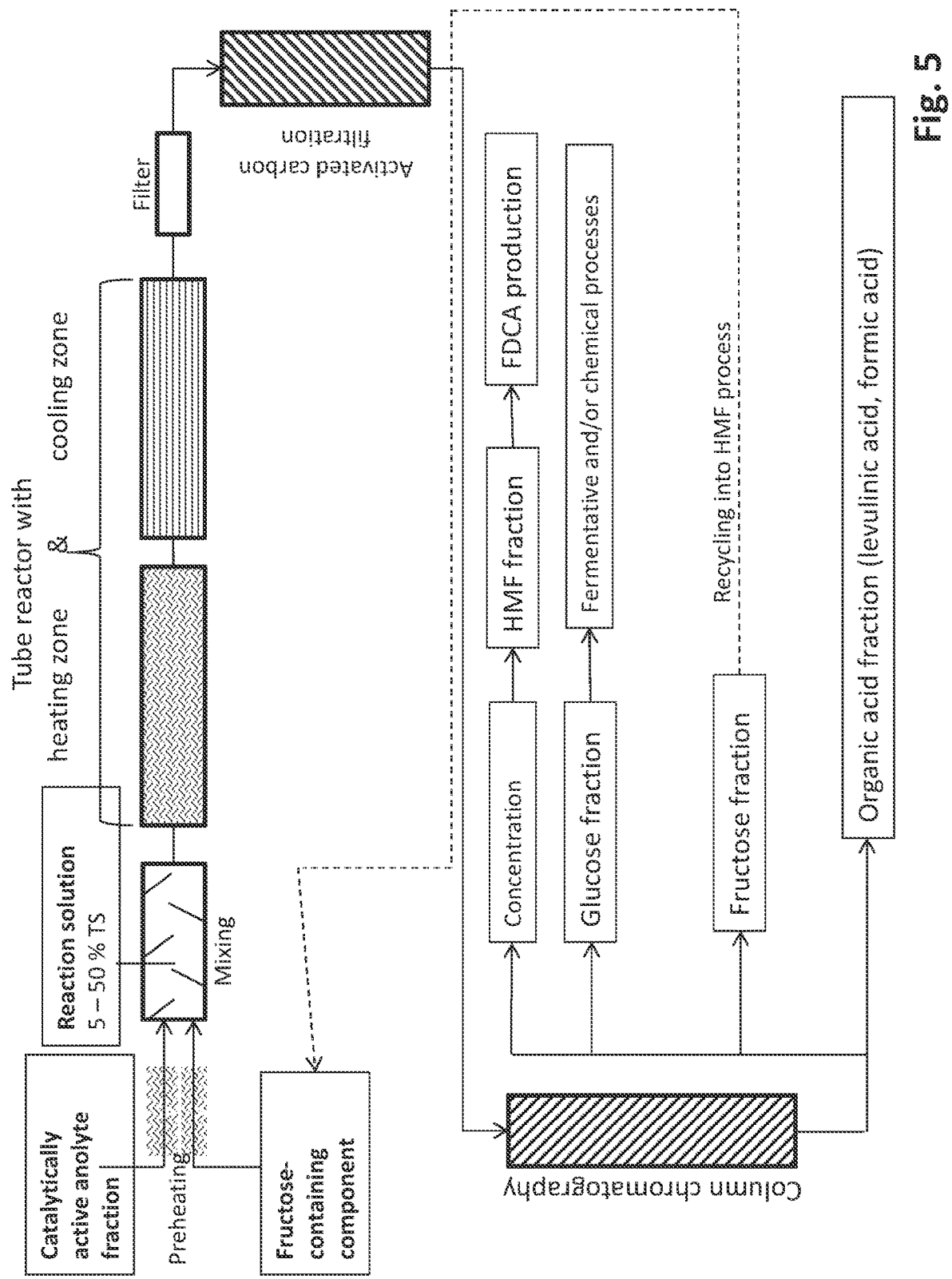
FIG. 5 is a schematic representation of the method according to the invention analogous to FIG. 4, wherein a column chromatographic separation is carried out in step h) and an HMF fraction, a glucose fraction, a fructose fraction and an organic acid fraction is obtained (step i)).

In the method according to the invention, a fructose-containing component which has a variable ratio of fructose to glucose and a catalytically active anolyte fraction are used as starting materials. The catalytically active anolyte fraction is produced in a water ionizer (Titanion SE Ultra) from deionized water mixed with the appropriate electrolyte. The fructose-containing component is mixed with the catalytically active anolyte fraction so that a reaction solution with a dry matter content of 20 to 40 wt.-% (DM carbohydrate based on the total weight of the reaction solution) is obtained. The reaction solution obtained in this way is pumped into the heated "heating zone" of the tubular reactor (outer diameter 8 mm, inner diameter 6 mm, length 630 mm) with the aid of an HPLC pump and is converted there. The tubular reactor is designed as a double-tube counterflow heat exchanger, wherein the temperature is controlled by means of a thermal oil in the outer jacket. The thermal oil is tempered by means of a thermostat. After the "heating zone"

there is a direct transition to the "cooling zone." This is also designed as a double-tube heat exchanger in counterflow (outer diameter of the product-carrying tube 8 mm, inner diameter 6 mm, length 125 mm). The reaction solution is cooled to room temperature within the "cooling zone" and the conversion is stopped. The product mixture is then filtered through a metal sintered filter (pore size 7 μm) and any insoluble humic substances that may have formed are removed. The pressure in the reactor system is set with the aid of a pressure holding valve so that boiling of the reaction solution and thus the occurrence of vapor bubbles is avoided (approx. 1 MPa at 180° C.).

The following examples show the implementation of the method according to the invention with different fructose-containing components, differently prepared catalytically active anolyte fractions, different DM contents and at different temperatures.

In all experiments, samples were taken during the test and analyzed by means of HPLC (BIORAD Aminex 87-H, 5 mmol/l sulfuric acid, 50° C.). The fructose conversion, HMF selectivity and the balance were then calculated from the analytical results (balance=(total of unconverted sugar, HMF and formic acid (in mol)*100/sugar used (in mol)). Levulinic acid is not taken into account in the balance, since one molecule of formic acid and one molecule of levulinic acid are produced from one molecule of HMF.

Example 1: HMF Synthesis with Catalytically Active Anolyte Fraction Based on 0.18% NaCl at 170° C. (MMR 112)

A fructose syrup with 95% fructose purity and a DM content of 70% was used as the fructose-containing component. The catalytically active anolyte fraction was produced from an electrolyte solution which contained 0.18 wt.-% of sodium chloride and which had a pH of 2.3. The fructose syrup was diluted with the catalytically active anolyte fraction to a DM content of 20% DM carbohydrate. This reaction solution was then converted with a residence time of 5.6 min in the heating zone at a temperature of 170° C. (temperature of the thermal oil).

Fructose conversion: 31.6%
HMF selectivity: 81.2%
Formic acid selectivity: 4.5%
Levulinic acid selectivity: 2.3%
Balance: 96%

Example 2: HMF Synthesis with Catalytically Active Anolyte Fraction Based on 0.625% NaCl at 170° C. (MMR 114)

A fructose syrup with 95% fructose purity and a DM content of 70% was used as the fructose-containing component. The catalytically active anolyte fraction was produced from an electrolyte solution which contained 0.625 wt.-% of sodium chloride and which had a pH of 2.3. The fructose syrup was diluted with the catalytically active anolyte fraction to a DM content of 20%/c DM carbohydrate. This reaction solution was then converted with a residence time of 5.6 min in the heating zone at a temperature of 170° C. (temperature of the thermal oil).

Fructose conversion: 35.0%
HMF selectivity: 80.6%
Formic acid selectivity: 5.2%
Levulinic acid selectivity: 2.3%
Balance: 95.6%

Example 3: HMF Synthesis with Catalytically Active Anolyte Fraction Based on 1% NaNO$_3$ at 165° C. (MMR 117)

A fructose syrup with 95% fructose purity and a DM content of 70% was used as the fructose-containing component. The catalytically active anolyte fraction was produced from an electrolyte solution which contained 1.0 wt.-% of sodium nitrate and which had a pH of 2.2. The fructose syrup was diluted with the catalytically active anolyte fraction to a DM content of 20% DM carbohydrate. This reaction solution was then converted with a residence time of 5.6 min in the heating zone at a temperature of 165° C. (temperature of the thermal oil).

Fructose conversion: 19.97%
HMF selectivity: 81.8%
Formic acid selectivity: 2.9%
Levulinic acid selectivity: 1.6%
Balance: 97.23%

Example 4: HMF Synthesis with Catalytically Active Anolyte Fraction Based on 0.25% NaNO$_3$ at 165° C. (MMR 117/2)

A fructose syrup with 95% fructose purity and a DM content of 70% was used as the fructose-containing component. The catalytically active anolyte fraction was produced from an electrolyte solution which contained 0.25 wt.-% of sodium nitrate and which had a pH of 2.2. The fructose syrup was diluted with the catalytically active anolyte fraction to a DM content of 20% DM carbohydrate. This reaction solution was then converted with a residence time of 5.6 min in the heating zone at a temperature of 165° C. (temperature of the thermal oil).

Fructose conversion: 16.5%
HMF selectivity: 86.5%
Formic acid selectivity: 3.1%
Levulinic acid selectivity: 1.5%
Balance: 98.6%

Example 5: HMF Synthesis with Catalytically Active Anolyte Fraction Based on 0.18% NaCl at 165° C. with 30% DM (MMR 137)

A fructose syrup with 85% fructose purity and a DM content of 75% was used as the fructose-containing component. The catalytically active anolyte fraction was produced from an electrolyte solution which contained 0.18 wt.-% of sodium chloride and which had a pH of 2.3. The fructose syrup was diluted with the catalytically active anolyte fraction to a DM content of 30% DM carbohydrate. This reaction solution was then converted with a residence time of 5.6 min in the heating zone at a temperature of 165° C. (temperature of the thermal oil).

Fructose conversion: 17.6%
HMF selectivity: 88.2%
Formic acid selectivity: 4.7%
Levulinic acid selectivity: 2.1%
Balance: 97.9%

Example 6: HMF Synthesis with Catalytically Active Anolyte Fraction Based on 0.18% NaCl at 165° C. with 40% DM (MMR 136)

A fructose syrup with 85% fructose purity and a DM content of 75% was used as the fructose-containing component. The catalytically active anolyte fraction was produced from an electrolyte solution which contained 0.18 wt.-% of sodium chloride and which had a pH of 2.3. The fructose syrup was diluted with the catalytically active anolyte fraction to a DM content of 40% DM carbohydrate. This reaction solution was then converted with a residence time of 5.6 min in the heating zone at a temperature of 165° C. (temperature of the thermal oil).

Fructose conversion: 15.5%

HMF selectivity: 89.7%

Formic acid selectivity: 5.5%

Levulinic acid selectivity: 1.6%

Balance: 98.2%

Example 7: Influence of the Fructose Purity on the HMF Selectivity in the HMF Synthesis with Catalytically Active Anolyte Fraction The fructose-containing components were fructose solutions with different fructose puritys (62%, 70%, 80%, 85%, 90% and 100%) and with a DM content of 30% in a catalytically active anolyte fraction. The catalytically active anolyte fraction was produced from an electrolyte solution which contained 0.18 wt.-% of sodium chloride and which had a pH of 2.3. These reaction solutions were then each converted with a residence time of 5.6 min in the heating zone at a temperature of 165° C. (temperature of the thermal oil).

| Fructose unit [%] | Fructose conversion [%] | HMF-Selectivity [%] | Formic acid selectivity [%] | Levulinic acid selectivity [%] | Balance [%] |
|---|---|---|---|---|---|
| 62 | 17.8 | 89.3 | 5.8 | 1.5 | 96.2 |
| 70 | 18.3 | 89.0 | 3.9 | 1.4 | 97.5 |
| 80 | 18.2 | 88.5 | 3.0 | 1.6 | 98.4 |
| 85 | 17.9 | 88.3 | 4.7 | 2.0 | 97.9 |
| 90 | 17.8 | 83.8 | 2.4 | 1.1 | 97.9 |
| 95 | 18.0 | 81.2 | 2.8 | 1.4 | 97.9 |
| 100 | 18.1 | 80.1 | 3.1 | 1.7 | 97.6 |

As the purity of the fructose increases, the selectivity to HMF deteriorates with the same conversion.

Example 8: Influence of the Cation in the Production of the Catalyticaly Active Anolyte Fraction on the HMF Selectivity in the HMF Synthesis A fructose syrup with a fructose purity of 85% and a DM content of 75% was used as the fructose-containing component. This syrup was diluted with a catalytically active anolyte fraction based on various chloride salts (lithium, sodium, potassium chloride, each 0.18 wt.-%) to a dry matter content of 30% carbohydrate.

These reaction solutions were then each converted with a residence time of 5.6 min in the heating zone at a temperature of 165° C. (temperature of the thermal oil).

| Electrolyte | pH value catalytically active anolyte fraction [-] | Chloride content catalytically active anolyte fraction [mg/l] | Fructose conversion [%] | HMF-Selectivity [%] | Formic acid selectivity [%] | Levulinic acid selectivity [%] | Balance [%] |
|---|---|---|---|---|---|---|---|
| LiCl | 2.2 | 1101 | 17.9 | 87.9 | 4.7 | 2.0 | 97.7 |
| NaCl | 2.3 | 793 | 17.6 | 88.2 | 4.7 | 2.1 | 97.9 |
| KCl | 2.3 | 645 | 17.2 | 86.8 | 2.9 | 1.1 | 97.9 |

Example 9: Comparative Experiment with 0.75% $H_2SO_4$ (without Catalytically Active Anolyte Fraction, State of the Art) at 135° C. and 30% DM (MMR 149)

A fructose syrup with a fructose purity of 85% and a DM content of 75% was used as the fructose-containing component. This syrup was set to a dry matter content of 30% carbohydrate with deionized water and treated with 0.75% sulfuric acid.

This reaction solution was then converted with a residence time of 5.6 min in the heating zone at a temperature of 135° C. (temperature of the thermal oil).

Fructose conversion: 20.0%

HMF selectivity: 73.2%

Formic acid selectivity: 9.15%

Balance: 96.1%

Example 10: Influence of the Chloride Concentration on Conversion and HMF Selectivity A fructose syrup with a fructose purity of 95% and a DM content of 75% was used as the fructose-containing component. This syrup was diluted to a dry matter content of 20% carbohydrate with catalytically active anolyte fractions based on different sodium chloride concentrations in the electrolysis (1.0 wt.-%, 0.625 wt.-%, 0.25 wt.-%, 0.18 wt.-%, 0, 10 wt.-% and 0.05 wt.-%).

These reaction solutions were then each converted with a residence time of 5.6 min in the heating zone at a temperature of 165° C. (temperature of the thermal oil).

| NaCl concentration during electrolysis [%] | Chloride concentration in the reaction solution during the HMB synthesis [mg/l] | Fructose conversion [%] | HMF selectivity [%] | Balance [%] |
|---|---|---|---|---|
| 1.0 | 4683 | 29.6 | 86.3 | 97.3 |
| 0.625 | 3272 | 30.5 | 85.1 | 97.2 |
| 0.25 | 1203 | 30 | 86.7 | 97.3 |
| 0.18 | 993 | 29.7 | 84.1 | 96.0 |
| 0.10 | 408 | 30.4 | 79.9 | 95.2 |
| 0.05 | 326 | 29.0 | 80.6 | 96.1 |

Fructose conversion and HMF selectivity are largely independent of the chloride concentration over a range.

Example 11: Effect of Electrolysis when Using DI and Tap Water

Within the scope of these experiments, a reaction solution with a dry matter content of 20% based on a fructose syrup with a fructose purity of 85% and an original dry matter content of 75% (F85/75) was prepared. For dilution, firstly pure deionized water or pure tap water was used, and secondly catalytically active anolyte fraction of deionized or tap water formed during the electrolysis was used. The resulting reaction solutions were then reacted in the heating zone with a residence time of 5.6 min at 169° C. Through regular sampling and analysis of the samples by means of HPLC, conversion and selectivities were monitored and a carbon balance was drawn up. Table 1 shows the results obtained.

TABLE 1

|  | Test | | | |
| --- | --- | --- | --- | --- |
|  | 2018MMR2 | 2018MMR4 | 2018MMR2 | 2017MMR166 |
| Dilution water | Deionized water | Anolyte fraction from deionized water | Tap water | Anolyte fraction from tap water electrolysis |
| pH value of the reaction solution [-] | 4.38 (pure deionized water 6.24) | 4.2 | 7.62 | 2.4 |
| Fructose conversion | 2.8 | 3.2 | 5.3 | 9.3 |
| HMF selectivity [%] | 76.3 | 84.6 | 29.2 | 82.8 |
| Levulinic acid selectivity [%] | 0 | 0 | 0 | 0.98 |
| Formic acid selectivity | 0 | 0 | 4.45 | 2.47 |
| Balance [%] | 99.4 | 99.5 | 98.0 | 98.5 |

The results show a clear improvement in terms of both fructose conversion and HMF and byproduct selectivity when using the respective anolyte fraction of deionized water and tap water compared to pure deionized or tap water.

Example 12: Effect of the Anolyte Fraction Concentration on the HMF Conversion

As part of this series of experiments, a catalytically active anolyte fraction was first produced on the basis of a 0.18% sodium chloride solution. Starting from this anolyte fraction (100% anolyte fraction), various dilutions were then made with pure DI water (75% anolyte fraction/25% DI water, 50% anolyte fraction/50% DI water and 25% anolyte fraction/75% DI water). These mixtures were then each used to prepare a reaction solution with a dry matter content of 20% DM based on a fructose syrup with 85% fructose purity and an original dry matter content of 75%, which was then processed under the same reaction conditions (residence time 5.6 min in the heating zone, temperature 169° C.) were converted. Through regular sampling and analysis of the samples by means of HPLC, conversion and selectivities were monitored and a carbon balance was drawn up. Table 2 shows the results obtained.

TABLE 2

|  | Test | | | |
| --- | --- | --- | --- | --- |
|  | 1 | 2 | 3 | 4 |
| Dilution water | 100% anolyte fraction | 75% anolyte fraction/25% deionized water | 50% anolyte fraction/50% deionized water | 25% anolyte fraction/75% deionized water |
| pH of the reaction solution [-] | 2.2 | 2.4 | 2.6 | 2.9 |
| Fructose conversion | 20.1 | 14.4 | 10.4 | 5.2 |
| HMF selectivity [%] | 87.9 | 89.0 | 91.9 | 100 |
| Levulinic acid selectivity [%] | 1.7 | 1.3 | 0.9 | 0 |
| Formic acid selectivity [%] | 3.3 | 1.6 | 2.2 | 0 |
| Balance [%] | 97.7 | 98.1 | 99.6 | 100 |

The results show a clear dependence of both the fructose conversion and the HMF and byproduct selectivities as well as the carbon balance on the concentration of the anolyte fraction. In comparison to pure deionized water or the anolyte fraction of deionized water (see Table 1), all experiments show a clear improvement, in particular with regard to the selectivity.

Example 13: Oxygen Content of Various Anolyte Fractions

Different anolyte fractions were produced and examined with regard to their oxygen content and pH value by means of an oxygen meter 4100e Mettler Toledo. For comparison, the oxygen content of fully demineralized water was determined.

| Solution | pH | Temperature | $O_2$ content (mg/l) |
| --- | --- | --- | --- |
| Deionized water | 6.24 | 21.3 | 9.3 |
| Anolyte fraction from deionized water | 3.0 | 23.1 | 19.4 |
| Anolyte fraction from 0.3 wt.-% $NaNO_3$ | 2.31 | 21 2 | 20.6 |
| Anolyte fraction from 0.5 wt.-% $NaNO_3$ | 1.98 | 21.5 | 27.5 |
| Anolyte fraction from 1.0 wt.-% $NaNO_3$ | 1.92 | 21 2 | 25.8 |
| Anolyte fraction from 2.0 wt.-% $NaNO_3$ | 1.87 | 22.2 | 25.6 |
| Anolyte fraction from 0.2 wt.-% NaCl | 2.14 | 21.5 | 19.4 |
| Anolyte fraction from 0.5 wt.-% NaCl | 1.98 | 21.6 | 26.81 |
| Anolyte fraction from 1.0 wt.-% NaCl | 2.02 | 21.4 | 24.2 |

The results shown in the table show that all anolyte fractions have a significantly higher oxygen content than non-electrolyzed, fully deionized water.

The invention claimed is:

1. A method for the production of 5-hydroxymethylfurfural (HMF) comprising the steps:
    a) providing a fructose-containing component,
    b) producing a catalytically active anolyte fraction by electrolysis of water,
    c) mixing the fructose-containing component and the catalytically active anolyte fraction to obtain a reaction solution,
    d) converting the fructose present in the reaction solution to HMF at a temperature of 90° C. to 200° C. to obtain a liquid HMF-containing product mixture, and
    e) obtaining a liquid HMF-containing product mixture.

2. The method of claim 1, wherein the water for the electrolysis is fully demineralized water.

3. The method of claim 1, wherein the water for the electrolysis comprises a salt selected from the group consisting of alkaline halides, alkaline earth halides, alkaline nitrates, alkaline earth nitrates, alkaline sulfates, alkaline earth sulfates, citrates, acetates, tartrates, oxalates, glycolates, gluconates and mixtures thereof.

4. The method according to claim 3, wherein the water for the electrolysis comprises 0.01 to 2.5 wt.-% of salt (based on the total weight of the water).

5. The method according to claim 1, wherein the pH of the catalytically active anolyte fraction is 1.5 to 4.5.

6. The method according to claim 1, wherein the fructose-containing component is a solid fructose-containing component or a liquid fructose-containing component.

7. The method according to claim 1, wherein in method step c) a reaction solution with a carbohydrate content of 5 to 50 wt.-% (dry matter carbohydrate in relation to the total weight of reaction solution) is obtained and used in method step d).

8. The method according to claim 1, wherein in method step c) a reaction solution with a fructose content of 40 to 100 wt.-% (dry matter fructose in relation to dry matter of the carbohydrate content of the reaction solution) is obtained and used in method step d).

9. The method according to claim 1, wherein the ratio of the carbohydrate content (dry matter) of the fructose-containing component to the catalytically active anolyte fraction (total weight) in the reaction solution is 0.01-2.5.

10. The method according to claim 1, wherein the ratio of fructose content (DM) of the fructose-containing component to catalytically active anolyte fraction (total weight) in the reaction solution is 0.01-2.5.

11. The method according to claim 1, wherein the fructose-containing component provided in step a), the anolyte fraction or both are set to a temperature of 90° C. to 200° C. before step c) or wherein the reaction solution obtained in step c) is set to a temperature of 90° C. to 200° C.

12. The method according to claim 1, wherein the process is carried out such that a fructose conversion of 1 to 50 mol-% is achieved in method step d).

13. The method according to claim 1, wherein the method is set so that in method step d) an HMF selectivity of 60 to 100 mol-% is obtained.

14. The method according to claim 1, wherein the method is carried out continuously.

15. The method according to claim 1, wherein apart from the catalytically active anolyte fraction, no further catalytically active component is used in the process.

16. The method according to claim 1, comprising the following step:
    f) cooling the liquid HMF product mixture to a temperature of 20 to 80° C.

17. The method according to claim 1, comprising the following step:
    g) filtration, decolorization and/or purification of the liquid HMF product mixture.

18. The method according to claim 1, comprising the following step:
    h) setting the liquid HMF product mixture to a dry matter content of 20 to 70 wt.-%.

19. The method according to claim 1, comprising the following steps:
    i) purification of the liquid HMF product mixture using chromatography, ultra- and/or nanofiltration, extraction with a suitable extractant, adsorption on a suitable material and subsequent targeted desorption and/or electrodialysis to separate at least one HMF fraction, and
    j) obtaining at least one HMF fraction.

20. The method according to claim 19, wherein the liquid HMF product mixture is separated in step i) using chromatography into at least four fractions comprising an HMF fraction, a glucose fraction, a fructose fraction and an organic acid fraction and in step j) at least an HMF fraction, a glucose fraction, a fructose fraction and an organic acid fraction is obtained.

21. The method according to claim 20, wherein the fructose fraction obtained in method step j) is recycled into step a).

22. The method according to claim 20, wherein the glucose fraction obtained in method step j) is used for the production of ethanol.

23. The method according to any of claim 20, wherein the organic acid fraction obtained in method step j) is used to isolate levulinic and formic acid.

24. The method according to claim 19, wherein the HMF fraction obtained in method step j) is oxidized directly and is oxidized in a further step to 2,5-furandicarboxylic acid (FDCA) without the need for further purification.

25. The method according to claim 1, wherein the pH of the catalytically active anolyte fraction is 2 to 3.

26. The method according to claim 1, wherein the fructose-containing component is fructose, a fructose syrup or a fructose solution.

* * * * *